United States Patent
Thieme et al.

(10) Patent No.: US 9,604,054 B2
(45) Date of Patent: Mar. 28, 2017

(54) DEVICE, SYSTEM, METHODS, AND COMPUTER READABLE MEDIA FOR MANAGING ACUTE AND CHRONIC PAIN

(71) Applicant: The University of North Carolina at Chapel Hill, Chapel Hill, NC (US)

(72) Inventors: Kati Thieme, Kirchhain (DE); Richard H Gracely, Durham, NC (US); William Maixner, Chapel Hill, NC (US); Olivier Georges Monbureau, Carrboro, NC (US)

(73) Assignee: THE UNIVERSITY OF NORTH CAROLINA AT CHAPE HILL, Chapel Hill, NC (US)

( * ) Notice: Subject to any disclaimer, the term of this patent is extended or adjusted under 35 U.S.C. 154(b) by 0 days.

(21) Appl. No.: 14/776,040

(22) PCT Filed: Mar. 13, 2014

(86) PCT No.: PCT/US2014/026579
§ 371 (c)(1),
(2) Date: Sep. 14, 2015

(87) PCT Pub. No.: WO2014/151860
PCT Pub. Date: Sep. 25, 2014

(65) Prior Publication Data
US 2016/0022988 A1 Jan. 28, 2016

Related U.S. Application Data

(60) Provisional application No. 61/784,475, filed on Mar. 14, 2013.

(51) Int. Cl.
*A61N 1/36* (2006.01)
*A61B 5/0452* (2006.01)
(Continued)

(52) U.S. Cl.
CPC ........ *A61N 1/36021* (2013.01); *A61B 5/0452* (2013.01); *A61N 1/08* (2013.01);
(Continued)

(58) Field of Classification Search
CPC .. A61N 1/08; A61N 1/36014; A61N 1/36021; A61N 1/36067; A61N 1/36071; A61B 5/0402; A61B 5/0452; A61B 5/0456
(Continued)

(56) References Cited

U.S. PATENT DOCUMENTS 4,331,157 A * 5/1982 Keller, Jr. .......... A61B 5/04004
600/509
4,938,223 A * 7/1990 Charters ............ A61N 1/36021
607/46
(Continued)

OTHER PUBLICATIONS

Graven-Nielsen, T. et al.: "Ketamine reduces muscle pain, temporal summation, and referred pain in fibromyalgia patients", Pain 85 (2000) 483-491.
(Continued)

*Primary Examiner* — Christopher A Flory
(74) *Attorney, Agent, or Firm* — NK Patent Law, PLLC

(57) ABSTRACT

Methods, devices, control modules, and computer readable media are provided for managing acute and chronic pain in subjects. More specifically, a method is provided for reducing pain in a subject that includes delivering to the subject a series of stimuli consisting of both painful and non-painful stimuli. A portion of each of the painful and the non-painful stimuli is delivered to the subject during a systolic phase of the subject's cardiac cycle and the remaining portion of each of the painful and the non-painful stimuli is delivered during a diastolic phase of the subject's cardiac cycle.

22 Claims, 13 Drawing Sheets

(51) Int. Cl.
*A61N 1/08* (2006.01)
*A61B 5/0402* (2006.01)
*A61B 5/00* (2006.01)
*A61B 5/0456* (2006.01)

(52) U.S. Cl.
CPC ........ *A61N 1/36014* (2013.01); *A61B 5/0402* (2013.01); *A61B 5/0456* (2013.01); *A61B 5/4836* (2013.01); *A61B 5/7285* (2013.01); *A61N 1/3615* (2013.01); *A61N 1/36067* (2013.01); *A61N 1/36071* (2013.01); *A61N 1/36075* (2013.01); *A61N 1/36082* (2013.01); *A61N 1/36171* (2013.01); *A61N 1/36178* (2013.01)

(58) Field of Classification Search
USPC .................................................. 607/2, 9, 46
See application file for complete search history.

(56) References Cited

U.S. PATENT DOCUMENTS

| | | | | |
|---|---|---|---|---|
| 5,193,537 A * | 3/1993 | Freeman | A61N 1/3625 | 607/10 |
| 5,205,284 A * | 4/1993 | Freeman | A61N 1/3625 | 607/10 |
| 5,492,132 A * | 2/1996 | Weinstein | A61B 5/0057 | 600/557 |
| 5,514,165 A * | 5/1996 | Malaugh | A61N 1/36021 | 607/2 |
| 5,782,880 A * | 7/1998 | Lahtinen | A61N 1/362 | 607/72 |
| 5,800,464 A * | 9/1998 | Kieval | A61N 1/3622 | 607/9 |
| 5,999,854 A * | 12/1999 | Deno | G06K 9/00496 | 607/18 |
| 6,312,393 B1 * | 11/2001 | Abreu | A61B 3/1241 | 600/558 |
| 6,333,342 B1 * | 12/2001 | Foster | C07D 211/90 | 514/356 |
| 6,832,982 B1 * | 12/2004 | Lapanashvili | A61N 1/36014 | 600/16 |
| 7,097,656 B1 * | 8/2006 | Akopov | A61B 18/203 | 606/10 |
| 7,635,337 B2 * | 12/2009 | Huiku | A61B 5/08 | 600/484 |
| 7,751,888 B1 * | 7/2010 | Schecter | A61N 1/3627 | 607/17 |
| 8,000,780 B2 * | 8/2011 | Wariar | A61B 5/02 | 600/508 |
| 8,660,648 B2 * | 2/2014 | Chavan | A61N 1/3605 | 607/44 |
| 9,295,843 B2 * | 3/2016 | Enrooth | A61N 1/362 | |
| 2002/0042563 A1 * | 4/2002 | Becerra | A61B 5/055 | 600/407 |
| 2002/0143369 A1 * | 10/2002 | Hill | A61N 1/36114 | 607/9 |
| 2003/0004549 A1 * | 1/2003 | Hill | A61N 1/36114 | 607/9 |
| 2003/0139678 A1 * | 7/2003 | Hoium | A61B 5/0472 | 600/510 |
| 2004/0049235 A1 * | 3/2004 | Deno | A61N 1/36114 | 607/9 |
| 2004/0116978 A1 * | 6/2004 | Bradley | A61N 1/36071 | 607/48 |
| 2005/0192637 A1 * | 9/2005 | Girouard | A61K 47/48992 | 607/3 |
| 2006/0004296 A1 * | 1/2006 | Huiku | A61B 5/02405 | 600/513 |
| 2006/0217615 A1 * | 9/2006 | Huiku | A61B 5/08 | 600/484 |
| 2006/0247699 A1 * | 11/2006 | Burnes | A61N 1/36114 | 607/9 |
| 2007/0060954 A1 * | 3/2007 | Cameron | A61N 1/0553 | 607/2 |
| 2007/0276453 A1 * | 11/2007 | Hill | A61N 1/36114 | 607/62 |
| 2007/0299477 A1 * | 12/2007 | Kleckner | A61N 1/36114 | 607/9 |
| 2008/0006281 A1 * | 1/2008 | Sih | A61M 37/00 | 128/899 |
| 2008/0280339 A1 * | 11/2008 | KenKnight | C12N 5/0657 | 435/173.4 |
| 2008/0280341 A1 * | 11/2008 | KenKnight | A61N 1/362 | 435/173.6 |
| 2009/0062883 A1 * | 3/2009 | Meadows | A61N 1/0553 | 607/46 |
| 2009/0240298 A1 * | 9/2009 | Lian | A61N 1/3627 | 607/9 |
| 2010/0042180 A1 * | 2/2010 | Mueller | A61N 1/0456 | 607/46 |
| 2010/0132058 A1 * | 5/2010 | Diatchenko | C12N 15/1137 | 800/9 |
| 2010/0145428 A1 * | 6/2010 | Cameron | A61N 1/0553 | 607/117 |
| 2010/0152804 A1 * | 6/2010 | Kleckner | A61N 1/36114 | 607/17 |
| 2011/0208264 A1 * | 8/2011 | Gliner | A61N 1/0531 | 607/45 |
| 2012/0253421 A1 * | 10/2012 | Gliner | A61N 1/0531 | 607/45 |
| 2012/0303084 A1 * | 11/2012 | Kleckner | A61N 1/36114 | 607/25 |
| 2013/0204144 A1 * | 8/2013 | Colborn | A61N 1/36082 | 600/483 |
| 2013/0218222 A1 * | 8/2013 | Doerr | A61N 1/368 | 607/17 |
| 2013/0244233 A1 * | 9/2013 | Diatchenko | C12N 15/1137 | 435/6.11 |

OTHER PUBLICATIONS

Maixner, W. et al.: "Relationship Between Pain Sensitivity and Resting Arterial Blood Pressure in Patients With Painful Temporomandibular Disorders", Psychosomatic Medicine 59:503-511 (1997).
Okifuji, A. et al.: "A Standardized Manual Tender Point Survey. I. Development and Determination of a Threshold Point for the Identification of Positive Tender Points in Fibromyalgia Syndrome", The Journal of Rheumatology 1997; 24:2, 377-383.
Berntson, G.G. et al.: "Heart rate variability: Origins, methods, and interpretive caveats", Psychophysiology, 34 (1997), 323-648.
Berrino, L. et al.: "Interaction between metabotropic and NMDA glutamate receptors in the periaqueductal grey pain modulatory system", Naunyn-Schmiedeberg's Arch Pharmacol (2001) 364 :437-443, DOI 10.007/s002100100477.
Bornhovd, K. et al.: "Painful stimuli evoke different stimulus-response functions in the amygdala, prefrontal, insula and somatosensory cortex: a single-trial fMRI study", Brain (2002), 125, 1326-1336.
Bruehl, S. et al.: "Interactions between the cardiovascular and pain regulatory systems: an updated review of mechanisms and possible alterations in chronic pain", Neuroscience and Biobehavioral Reviews 28 (2004) 395-414.
Bruehl, S. et al.: "Altered Cardiovascular/Pain Regulatory Relationships in Chronic Pain", International Journal of Behavioral Medicine, 5(1), 63-75, 1998.
Burgmer, M. et al.: "Cerebral mechanisms of experimental hyperalgesia in fibromyalgia", Eur J Pain 16 (2012) 636-647.
Diers, M. et al.: "Treatment-related changes in brain activation in patients with fibromyalgia syndrome", Exp Brain Res (2012) 218:619-628, DOI 10.1007/s00221-012-3055-2.
Ditto, B. et al.: "Carotid Baroreflex Sensitivity at Rest and During Psychological Stress in Offspring of Hypertensives and Non-Twin Sibling Pairs", Psychosomatic Medicine 52:610-620 (1990).

(56) References Cited

OTHER PUBLICATIONS

Edwards, L. et al.: "Pain-related evoked potentials are modulated across the cardiac cycle", Pain 137 (2008) 488-494.
Elbert, T. et al.: "Baroreceptor Stimulation Alters Pain Sensation Depending on Tonic Blood Pressure", Psychophysiology, vol. 25, No. 1, 1988, 25-29.
Elbert, T et al.: "Sensory Effects of Baroreceptor Activation and Perceived Stress Together Predict Long-Term Blood Pressure Elevations", International Journal of Behavioral Medicine 1 (1994), 3, pp. 215-228.
Elbert, T. et al.: "Chaos and Physiology: Deterministic Chaos in Excitable Cell Assemblies", Physiological reviews, vol. 74, No. 1, Jan. 1994.
Flor, H. et al: "Acquisition of Chronic Pain: Psychophysiological Mechanisms", APS Journal 3(2): 119-127, 1994.
Flor, H. et al: "The role of operant conditioning in chronic pain: an experimental investigation", Pain 95 (2002) 111-118.
Fridlund, A. J. et al.: "Guidelines for Human Electromyographic Research", Psychophysiology, vol. 23, No. 5, 1986, 567-589.
Gracely, R. H. et al.: "Functional Magnetic Resonance Imaging Evidence of Augmented Pain Processing in Fibromyalgia", Arthritis & Rheumatism, vol. 46, No. 5, May 2002, pp. 1333-1343, DOI 10.1002/art.10225.
Jennings, J. R. et al.: "Publication Guidelines for Heart Rate Studies in Man", Psychophysiology, vol. 18, No. 3, 1981, 226-231.
Jensen, K. B. et al.: "Cognitive Behavioral Therapy increases pain-evoked activation of the prefrontal cortex in patients with fibromyalgeia", Pain 153 (2012) 1495-1503.
Kircher, T. et al.: "Effect of Cognitive-Behavioral Therapy on Neural Correlates of Fear Conditioning in Panic Disorder", Biol Psychiatry 2013;73:93-101.
Ku, Y.-H. et al.: "Role of Corticotropin-Releasing Factor and Substance P in Pressor Responses of Nuclei Controlling Emotion and Stress", Peptides, vol. 19, No. 4, pp. 677-682, 1998, Pll S0196-9781(98)00004-7.
Lawler, J. E. et al.: "Baroreflex Function in Chronically Stressed Borderline Hypertensive Rats", Physiology & Behavior, vol. 49, pp. 539-542, 1991.
Maixner, W. et al.: "Sensitivity of patients with painful temporomandibular disorders to experimentally evoked pain", Pain, 63 (1995) 341-351.
Maixner, W.: "Interactions Between Cardiovascular and Pain Modulatory Systems: Physiological and Pathophysiological Implications", Journal of Cardiovascular Electrophysiology vol. 2, No. 2. Supplement, Apr. 1991.
McIntyre, D. et al.: "Systolic inhibition of nociceptive responding is moderated by arousal", Psychophysiology, 43 (2006), 314-319, DOI: 10.1111/J.1469-8986.2006.00407.x.
Mitchell, V. P. et al: "Norepinephrine Content of Discrete Brain Nuclei in Acutely and Chronically Stressed Borderline Hypertensive Rats", Brain Research Bulletin. vol. 22, pp. 545-541, 1989.
Moher, D. et al.: "The CONSORT statement: revised recommendations for improving the quality of reports of parallel group randomized trials", BMC Medical Research Methodology (2001) 1:2.
Pertovaara, A.: "A Neuronal Correlate of Secondary Hyperalgesia in the Rat Spinal Dorsal Horn Is Submodality Selective and Facilitated by Supraspinal Influence", Experimental Neurology 149, 193-202 (1998), Article No. EN976688.
Qian, Z. M. et al.: "Central ANG II Receptor Involved in Carotid Sinus Reflex Reselling in Chronically Stressed Rats", Physiology & Behavior, vol. 62, No. 2, pp. 241-247, 1997, PII S0031-9384(97)00109-1.

Randich, A. et al.: "Interactions Between Cardiovascular and Pain Regulatory Systems", Neuroscience & Biobehavioral Reviews, vol. 8, pp. 343-367, 1984.
Rau, H. et al.: "Psychophysiology of arterial baroreceptors and the etiology of hypertension", Biological Psychology 57 (2001), pp. 179-201.
Rau, H. et al.: "Baroreceptor stimulation alters cortical activity", Psychophysiology 30 (1993), 3, pp. 122-325.
Rutecki, P.: "Anatomical, Physiological, and Theoretical Basis for the Antiepileptic Effect of Vagus Nerve Stimulation", Epilepsia, 31(Suppl. 2):S1-S6, 1990.
Seagard, J. L. et al.: "Modulation of the carotid baroreceptor reflex by substance P in the nucleus tractus solitarius", Journal of the Autonomic Nervous System 78 (2000) 77-85.
Seminowicz, D.A. et al.: "Cognitive modulation of pain-related brain responses depends on behavioral strategy", Pain 112 (2004) 48-58.
Staud, R. et al.: "Maintenance of windup of second pain requires less frequent stimulation in fibromyalgia patients Compared to normal controls", Pain 110 (2004) 689-696.
Steptoe, A. et al.: "Assessment of Baroreceptor Reflex Function During Mental Stress and Relaxation", Psychophysiology, vol. 26, No. 2, 1989, 140-147.
Steriade, M.: "New vistas on the morphology, chemical transmitters and physiological actions of the ascending brainstem reticular system", Archives Italiennes de Biologie, 126: 225-238, 1988.
Thieme, K. et al.: "Heterogeneity of psychophysiological stress responses in fibromyalgia syndrome patients", Arthritis Research & Therapy 2006, 8:R9 (doi:10.1186/ar1863).
Thieme, K. et al.: "Psychological pain treatment in fibromyalgia syndrome: efficacy of operant behavioural and cognitive behavioural treatments", Arthritis Research & Therapy 2006, 8:R121 (doi:10.1186/ar2010).
Thieme, K. et al.: "Responder Criteria for Operant and Cognitive-Behavioral Treatment of Fibromyalgia Syndrome", Arthritis & Rheumatism (Arthritis Care & Research), vol. 57, No. 5, Jun. 15, 2007, pp. 830-836, DOI 10.1002/art.22778.
Vlaeyen, J. W. et al.: "Behavioural rehabilitation of chronic low back pain: Comparison of an operant treatment, an Operant-cognitive treatment and an operant-respondent treatment", British Journal of Clinical Psychology (1995), 34, 35-118.
Watkins, L. L. et al.: "Association of anxiety with reduced baroreflex cardiac control in patients after acute myocardial infarction", American Heart Journal, vol. 143, No. 3, Mar. 2002.
Watkins, L. R. et al.: "Implications of immune-to-brain communication for sickness and pain", Proc. Natl. Acad. Sci. USA, vol. 96, pp. 7710-7713, Jul. 1999.
Wiertelak, E.P. et al.: "Comparison of the effects of nucleus tractus solitarius and ventral medial medulla lesions on illness-induced and subcutaneous formalin-induced hyperalgesias", Brain Research 748 (1997) 143-150.
Wolfe, F. et al.: "Fibromyalgia Criteria and Severity Scales for Clinical and Epidemiological Studies: A Modification of the ACR Preliminary Diagnostic Criteria for Fibromyalgia", The Journal of Rheumatology 2011; 38:6; doi:10.3899/rheum.100594.
Wolfe, F. et al.: "The American College of Rheumatology 1990 Criteria for the Classification of Fibromyalgia", Arthritis and Rheumatism, vol. 33, No. 2, Feb. 1990, 160-172.
Woolf, C. J: "Central sensitization: Implications for the diagnosis and treatment of pain", Pain. Mar. 2011 ; 152(3 Suppl): S2-15. doi:10.1016/j.pain.2010.09.030.
Steriade, M. et al.: "The Functional States of the Thalamus and the Associated Neuronal Interplay", Physiological Reviews, 1988, 68: 649-742.
Thieme, K. et al.: "Operant Behavioral Treatment of Fibromyalgia: A Controlled Study", Arthritis Rheum 2003, 49:314-320.
Banic, B. et al.: "Evidence for spinal cord hypersensitivity in chronic pain after whiplash injury and in fibromyalgia", Pain 107 (2004) 7-15.

* cited by examiner

DEVICE, SYSTEM, METHODS, AND COMPUTER READABLE MEDIA FOR MANAGING ACUTE AND CHRONIC PAIN

CROSS REFERENCE TO RELATED APPLICATIONS

This application is a C.F.R. section 371 national phase application of International Patent Application No. PCT/US14/26579 filed on Mar. 13, 2014, which claims the benefit of U.S. provisional patent application No. 61/784,475 filed Mar. 14, 2013, the disclosures of which are each hereby incorporated by reference in their entireties.

FEDERAL FUNDING LEGEND

This invention was made with government support under Grant No. R01-Ar054895-01A1 awarded by the National Institutes of Health. The government has certain rights in the invention.

TECHNICAL FIELD

The present disclosure relates to methods, devices, control modules, and computer readable media for managing acute and chronic pain.

BACKGROUND

The 1990 research criteria for Fibromyalgia syndrome (FM) characterized this disorder by the presence of widespread pain combined and tenderness at 11 or more of 18 specific 'tender points'. These criteria have been used for clinical diagnosis until the development of recent criteria that include the Widespread Pain Index (WPI) and the Symptom Severity (SS) scale that evaluates symptoms such as fatigue, sleep impairment and different autonomic symptoms (Wolfe et al., 1990, 2011). There is no consensus regarding the various mechanisms underlying the set of symptoms reported by FM sufferers.

An emerging body of evidence provides support for an important interaction between pain processing and cardiorespiratory regulatory systems (Bruehl & Chung, 2004; Maixner, 1991; Randich & Maixner, 1984; Maixner et al., 1995). It is generally accepted that the stimulation of carotid sinus and cardiopulmonary baroreceptor afferents, which are activated by dynamic changes in cardiovascular and respiratory parameters, reduce the magnitude of perceived pain. This attenuation of pain is mediated by activation of endogenous pain inhibitory systems, including central nervous system processes that inhibit activity in the ascending reticular activating system (ARAS), a non-specific cortical projecting system. The ARAS plays an important role in sculpting sensory, motor, and autonomic responses to somatosensory input (Steriade 1988, Steriade and Llinas 1988). In healthy individuals, a functional interaction of the cardiovascular and pain regulatory systems has been established whereby elevation in resting arterial blood pressure is related to reduction in pain sensitivity. The activation of carotid sinus and cardiopulmonary afferents attenuates perceived pain.

Recent studies have also shown that persistent pain conditions may be mediated in part by impairments in this interaction between blood pressure and pain sensitivity (Thieme & Turk, 2006). Diminished baroreceptor sensitivity may have an important impact on pain chronicity (Maixner 1997; Bruehl & Chung, 2004); Bruehl et al., 1998).

It is desired to provide non-pharmacological methods and devices for reducing chronic and acute pain.

SUMMARY

In one aspect of the present disclosure, a method is provided for reducing pain in a subject comprising: delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle.

In one aspect of the present disclosure, a method is provided for reducing pain in a subject comprising: delivering to a subject with a stimulator a series of stimuli, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during a diastolic phase of the subject's cardiac cycle.

In one aspect of the present disclosure, a device is provided, comprising: a sensor for measuring cardiac cycle configured to indicate a systolic phase and a diastolic phase of a subject's cardiac cycle; a stimulator configured to deliver a stimulus to the subject; and a control module in communication with the sensor for measuring cardiac cycle and the stimulator, the control module configured to: direct the stimulator to deliver a series of the stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect of the present disclosure a device is provided, comprising: a sensor for measuring cardiac cycle configured to indicate a systolic phase and a diastolic phase of a subject's cardiac cycle; a stimulator configured to deliver a stimulus to the subject; and a control module in communication with the sensor for measuring cardiac cycle and the stimulator, the control module configured to: direct the stimulator to deliver a series of the stimuli to the subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle.

In one aspect of the present disclosure a control module is provided, the control module in communication with a sensor for measuring cardiac cycle configured to indicate a systolic phase and a diastolic phase of the subject's cardiac cycle and a stimulator, the control module configured to: direct the stimulator to deliver to a subject a series of stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect of the present disclosure, a control module is provided, the control module in communication with a sensor for measuring cardiac cycle configured to indicate a systolic phase and a diastolic phase of the subject's cardiac cycle and a stimulator, the control module configured to: direct the stimulator to deliver a series of stimuli to a subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle.

In one aspect, a computer program product is provided for reducing pain in a subject, comprising: a computer readable storage medium having computer readable program code embodied therewith, the computer readable program code comprising: computer readable program code configured to: receive a response signal from a sensor for measuring cardiac cycle that indicates a systolic phase and a diastolic phase of a subject's cardiac cycle; and direct a stimulator to deliver to the subject a series of stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect of the present disclosure, a computer program product is provided for reducing pain in a subject, comprising: a computer readable storage medium having computer readable program code embodied therewith, the computer readable program code comprising: computer readable program code configured to: receive a response signal from a sensor for measuring cardiac cycle that indicates a systolic phase and a diastolic phase of a subject's cardiac cycle; direct a stimulator to deliver a series of stimuli to the subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle.

In one aspect of the present disclosure a method is provided to facilitate pharmacotherapy, the method comprising: delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle, wherein the subject's pharmacotherapy is facilitated.

In one aspect of the present disclosure a method is provided to facilitate non-pharmacological therapies, the method comprising: delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle, wherein the subject's non-pharmacological therapies are facilitated.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed.

DETAILED DESCRIPTION

The presently disclosed subject matter is described with specificity to meet statutory requirements. However, the description itself is not intended to limit the scope of this patent. Rather, the inventor has contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

The terms "baroreceptor" and "baroreflex" are herein used interchangeably for the purposes of the specification and claims.

In one aspect, the presently disclosed subject matter provides methods, devices, control modules, and computer readable media for the management of acute and chronic pain by delivery of painful and non-painful stimuli during different phases of a patient's cardiac cycle. The delivery of stimuli to a subject during the systolic phase of the cardiac cycle according to the present disclosure can produce a profound long lasting analgesic effect in patients with pain such as, for example, in patients with fibromyalgia. The methods, devices, control modules, and computer readable media of the present disclosure can be useful in treating both acute and chronic pain conditions.

Figure 12:
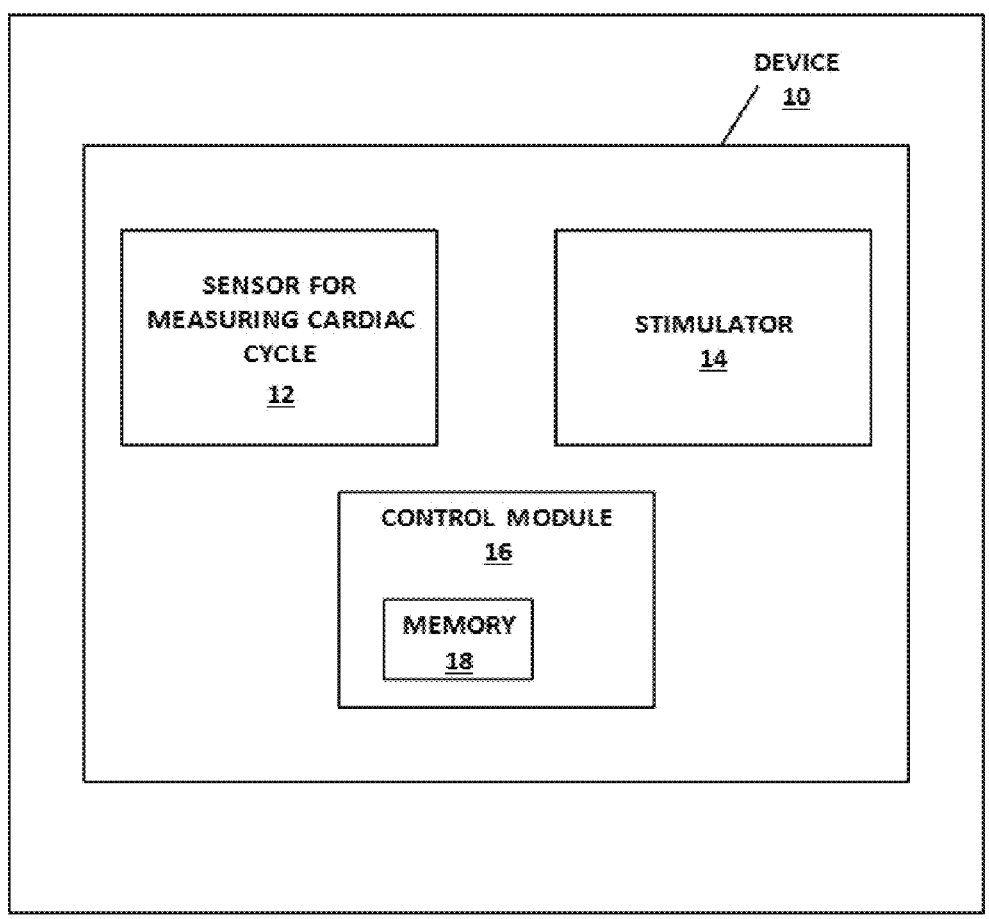
FIG. 12 is a block diagram of a device in accordance with one or more embodiments of the present disclosure.

A device 10 in accordance with one or more embodiments of the present subject matter is shown in FIG. 12. The device 10 comprises a sensor 12 for measuring a subject's cardiac cycle and configured to indicate a systolic phase and a diastolic phase of the cardiac cycle, a stimulator 14 for delivery of a stimulus to a subject, and a control module 16 in communication with the sensor 12 and the stimulator 14. The device 10 comprises memory 18 embedded within the control module 16.

Figure 13:
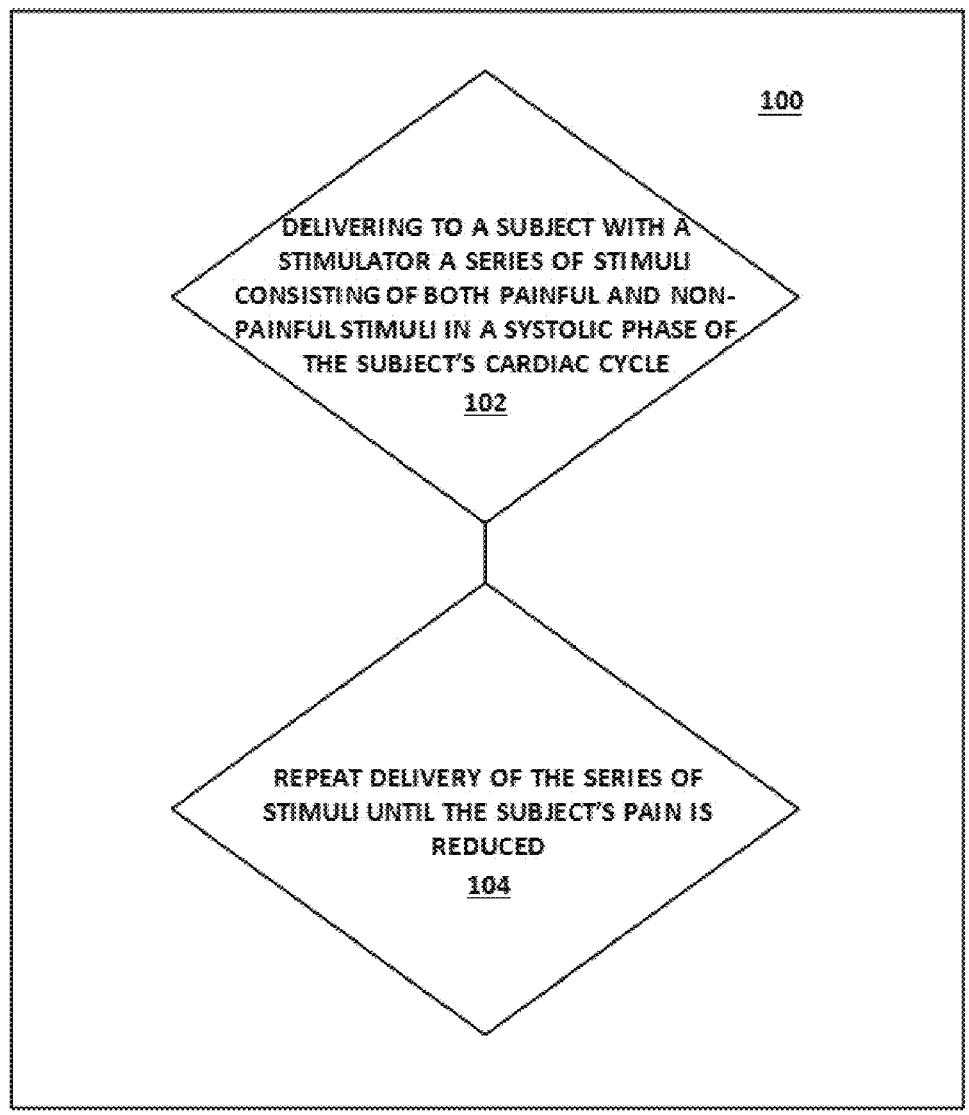
FIG. 13 is a flow diagram of a method in accordance with one or more embodiments of the present disclosure.

FIG. 13 shows a flow diagram 100 of a method for reducing pain in a subject in accordance with one or more embodiments of the present subject matter. A method is provided for reducing pain in a subject, the method according to flow diagram 100 including delivering to a subject with a stimulator a series of stimuli consisting of both painful and non-painful stimuli in a systolic phase of the subject's cardiac cycle, until the subject's pain is reduced, as shown in the flow diagram at 102. The method can further comprise repeating delivery of the series of stimuli as shown in the flow diagram at 104, until the subject's pain is reduced.

The methods, devices, control modules, and computer readable media can be applicable for conditions that are currently treated by TENS (transcutaneous electrical nerve stimulation). The stimuli can be delivered during specific time periods of the cardiac cycle such that treatment effects are maximized. Thus, in one aspect the presently disclosed subject matter can be useful as a non-pharmacological modality for treating acute and chronic pain. In another aspect, the present subject matter can be useful for facilitating pharmacotherapy in a subject. For example, methods are provided to facilitate pharmacotherapy by one or more of enabling reduced dose of chemotherapy in patients with melanoma, enabling reduced dose of antiepileptic drugs in patients with epilepsy, enabling reduced dose of anti-inflammatory drugs in patients with arthritis, enabling reduced dose of sleep-inducing drugs for patients with sleep apnea, enabling reduced dose of detoxification drugs (such as for example clonidine an naltrexone) in patients with chronic pain and opioid addiction, enabling reduced dose of anesthesia during surgery, including patients with surgery phobia, or enabling reduced dose of blood pressure-lowering drugs in patients with hypertension, or enabling reduced dose of anti-anxiety drugs in patients with anxiety.

In one aspect, the present disclosure provides methods for reducing pain in a subject including delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle.

In one aspect, the present disclosure provides methods for reducing pain in a subject including delivering to a subject with a stimulator a series of stimuli consisting of both painful and non-painful stimuli, through the spinal nerves and otherwise into the brain, wherein a portion of each of the painful and the non-painful stimuli is delivered during a systolic phase of the subject's cardiac cycle and the remaining portion of each is delivered during a diastolic phase of the subject's cardiac cycle.

In one aspect, the present disclosure provides methods for reducing pain in a subject including delivering to a subject with a stimulator a series of stimuli, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during a diastolic phase of the subject's cardiac cycle. The method can further include repeating one or more times delivering to the subject the series of stimuli, until the subject's pain is reduced. The method can further include repeating one or more times delivering to the subject the series of stimuli, wherein the stimuli having the non-painful threshold and greater than 50% of the pain tolerance are re-determined for the subject prior to the repeating delivery, until the subject's pain is reduced.

The order of delivery of the stimuli to the subject can be unpredictable to the subject. The order of delivery of the stimuli to the subject can be predictable to the subject.

The subject can be characterized by one or more of fibromyalgia syndrome, migraine, osteoarthritis, low back pain, inflammatory arthritis, rheumatoid arthritis, or Parkinson's. The subject can be characterized by one or more of anxiety or hypertension. The subject can be characterized by a condition that is treatable by transcutaneous electrical nerve stimulation (TENS). The pain can be chronic pain or acute pain.

The route of administration of the stimuli can be surface administration. The stimuli can be delivered to one or more digits of the subject's hands. The device of the present disclosure can be an implantable device. The route of administration of the stimuli can be subcutaneous administration. The route of administration of the stimuli can be direct nerve administration. The route of administration of the stimuli can be near, direct or indirect to one or more nerves or baroreceptors, through spinal or cranial nerves to the perception mechanism of the brain.

The stimulus can be characterized by a fast rate of onset and offset. The series of stimuli can be delivered at a low-frequency of stimulation (0.2 HZ). The series of stimuli can be delivered over an 8 minute period The portion of each of the non-painful stimuli and the greater than 50% of the pain tolerance stimuli delivered during the systolic phase can be one half. The stimuli delivered during the systolic phase of the cardiac cycle can be delivered at a 20% value of an average inter-beat-interval and the stimuli delivered during the diastolic phase of the cardiac cycle can be delivered at an 80% value of an average inter-beat-interval.

The stimulus can be selected from the group consisting of an electrical pulse stimulus, a punctate stimulus, and a laser stimulus. The stimulus can comprise an electrical pulse stimulus, a punctate stimulus, or a laser stimulus, and combinations thereof. The stimulus can be any stimulus which causes pain impulses to move through the spinal cord and/or increases the blood pressure, heart rate or respiration rate (HRT) of the subject. The stimulus can be an electrical pulse stimulus and the parameters of electrical stimulation—current level, pulse duration, and pulse frequency can be variable and the delivery of electrical stimuli can be triggered and time gated relative to a systolic and a diastolic phase of the subject's cardiac cycle. A sensor can be used to measure the subject's cardiac cycle and to indicate the systolic and diastolic phase of the subject's cardiac cycle. In one example, the sensor is an electrocardiogram and the R-wave of the electrocardiogram is used to trigger the delivery of defined electrical pulse within specified time windows of the cardiac cycle.

The stimulus can be an electrical pulse stimulus delivered as a train consisting of multiple individual electrical pulses of the same amplitude. The train can consist of 10 individual 7 msec electrical pulses delivered over a 250 msec period with an interpulse interval of 27 msec. The fraction of the stimuli below the non-painful threshold can be one-third and the fraction of the stimuli having greater than 50% of the pain tolerance can be one-third having 50% of the pain tolerance and one-third having 75% of the pain tolerance. The portion of each of the stimuli below the non-painful threshold, having 50% of the pain tolerance, and having 75% of the pain tolerance delivered during the systolic phase can be one half.

The stimulus can be an electrical pulse stimulus delivered as a train consisting of 10 individual 7 msec electrical pulses of the same amplitude delivered over a 250 msec period with an interpulse interval of 27 msec, and the method can further include prior to delivering the series of stimuli to the subject, delivering to the subject with the stimulator multiple of the trains in an ascending intensity, wherein the pulses in a first train can have an amplitude of 200 µA, wherein one or more subsequent trains can have an incremental increase in amplitude of 200 µA up to a maximum amplitude of 10000 µA, and wherein after each train the subject can be queried for the subject's perception of the intensity of the train such that the subject's non-painful threshold and pain tolerance are determined. The method can further include repeating one or more times the delivering to the subject the multiple trains of ascending intensity such that an average for each of the subject's non-painful threshold and pain tolerance is determined.

Without being limited to any one mechanism, the data provided herein indicate that the methods of the present disclosure can result in a diminishment of sympathetic activity. Such a diminishment of sympathetic activity can lead to a restoration of the physiological balance of the autonomic nervous system (parasympathetic and sympathetic) and an improvement in the clinical signs and symptoms of diseases and disorders influenced by reduced sympathetic and/or an increased parasympathetic activity. Thus, the method of the present disclosure can decrease the sympathetic tone, especially over time, which tone tends to be high for chronic pain subjects.

In one aspect, the present disclosure provides a device that includes a sensor for measuring cardiac cycle configured to indicate a systolic phase and a diastolic phase of a subject's cardiac cycle; a stimulator configured to deliver a stimulus to the subject; and a control module in communication with the sensor for measuring cardiac cycle and the stimulator, the control module is configured to: direct the stimulator to deliver a series of the stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect, the present disclosure provides a device that includes a sensor for measuring cardiac cycle configured to indicate a systolic phase and a diastolic phase of a subject's cardiac cycle; a stimulator configured to deliver a stimulus to the subject; and a control module in communication with the sensor for measuring cardiac cycle and the stimulator, the control module configured to: direct the stimulator to deliver a series of the stimuli to the subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle.

The control module can be configured to direct the stimulator to repeat one or more times the deliver function of the series of stimuli to the subject, until the subject's pain is reduced.

The control module can be configured to direct the stimulator to repeat one or more times the deliver function to the subject the series of stimuli, wherein the stimuli having the non-painful threshold and having greater than 50% of the pain tolerance are re-determined for the subject prior to the repeated deliver function, until the subject's pain is reduced.

In one aspect of the device, the stimulus can be an electrical pulse stimulus delivered as a train consisting of 10 individual 7 msec electrical pulses of the same amplitude delivered over a 250 msec period with an interpulse interval of 27 msec, and the control module can be further configured to: prior to the direct to deliver function of the series of stimulito the subject, direct the stimulator to deliver to the subject multiple of the trains in an ascending intensity, wherein the pulses in a first train have an amplitude of 200 µA, wherein one or more subsequent trains have an incremental increase in amplitude of 200 µA up to a maximum amplitude of 10000 µA, and wherein after each train the subject is queried for the subject's perception of the intensity of the train such that the subject's non-painful threshold and pain tolerance are determined.

In one aspect of the device, the control module can be further configured to repeat one or more times the direct to deliver function of the multiple trains of the ascending intensity such that an average for each of the subject's non-painful threshold and pain tolerance is determined.

In one aspect of the device, the sensor for measuring cardiac cycle can be an electrocardiogram, a photoplethysmographic sensor, an acoustic sensor, a respiratory cycle sensor, a pressure sensor, or other means of determining the time of the heart beat R-wave.

In one aspect, the present disclosure provides a control module in communication with a sensor for measuring cardiac cycle configured to indicate a systolic phase and a diastolic phase of the subject's cardiac cycle and a stimulator, the control module is configured to: direct the stimulator to deliver to a subject a series of stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect, the present disclosure provides a control module in communication with a sensor for measuring cardiac cycle configured to indicate a systolic phase and a diastolic phase of the subject's cardiac cycle and a stimulator, the control module is configured to: direct the stimulator to deliver a series of stimuli to a subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle. The control module can be configured to direct the stimulator to repeat one or more times the deliver function of the series of stimuli to the subject, until the subject's pain is reduced. The control module can be configured to direct the stimulator to repeat one or more times the deliver function of the series of stimuli to the subject, wherein the stimuli having the non-painful threshold and greater than 50% of the pain tolerance are re-determined for the subject prior to the repeated deliver function, until the subject's pain is reduced.

In one aspect of the control module, the stimulus can be an electrical pulse stimulus delivered as a train consisting of 10 individual 7 msec electrical pulses of the same amplitude delivered over a 250 msec period with an interpulse interval of 27 msec, and the control module can be further configured to: prior to the direct to deliver function of the series of stimuli to the subject, direct the stimulator to deliver to the subject multiple of the trains in an ascending intensity, wherein the pulses in a first train have an amplitude of 200 µA, wherein one or more subsequent trains have an incremental increase in amplitude of 200 µA up to a maximum amplitude of 10000 µA, and wherein after each train the subject is queried for the subject's perception of the intensity of the train such that the subject's non-painful threshold and pain tolerance are determined. The control module can be further configured to: to repeat one or more times the direct to deliver function of the multiple trains of the ascending intensity such that an average for each of the subject's non-painful threshold and pain tolerance is determined.

In one aspect, the present disclosure provides a computer program product for reducing pain in a subject, comprising: a computer readable storage medium having computer readable program code embodied therewith, the computer readable program code includes computer readable program code configured to: receive a response signal from a sensor for measuring cardiac cycle that indicates a systolic phase and a diastolic phase of a subject's cardiac cycle; and direct a stimulator to deliver to the subject a series of stimuli consisting of both painful and non-painful stimuli, wherein a portion of each of the painful and the non-painful stimuli is delivered during the systolic phase of the subject's cardiac cycle and the remaining portion of each is delivered during the diastolic phase of the subject's cardiac cycle.

In one aspect, the present disclosure provides a computer program product for reducing pain in a subject, including: a computer readable storage medium having computer readable program code embodied therewith, the computer readable program code includes: computer readable program code configured to: receive a response signal from a sensor for measuring cardiac cycle that indicates a systolic phase and a diastolic phase of a subject's cardiac cycle; direct a stimulator to deliver a series of stimuli to the subject, wherein at least a fraction of the stimuli are below a non-painful threshold for the subject and at least a fraction of the stimuli are greater than 50% of a pain tolerance for the subject, and wherein a portion of each of the non-painful stimuli and the greater than 50% of the pain tolerance stimuli is delivered during the systolic phase of the subject's cardiac cycle and the remaining portion of each is delivered during the diastolic phase of the subject's cardiac cycle.

The computer readable program code can be further configured to direct the stimulator to repeat one or more times the deliver function of the series of stimuli to the subject, until the subject's pain is reduced.

The computer readable program code can be further configured to direct the stimulator to repeat one or more times the deliver function of the series of stimuli to the subject, wherein the stimuli having the non-painful threshold and the greater than 50% of the pain tolerance are re-determined for the subject prior to the repeated deliver function, until the subject's pain is reduced.

In one aspect, the present disclosure provides a method to facilitate pharmacotherapy, the method including delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle.

The method for facilitating pharmacotherapy can further include repeating one or more times delivering to the subject the series of stimuli, until pharmacotherapy is facilitated for the subject.

The method for facilitating pharmacotherapy can further include: repeating one or more times the delivering to the subject the series of stimuli, wherein the painful and the non-painful stimuli are re-determined for the subject prior to the repeating delivery, until pharmacotherapy is facilitated for the subject.

The method for facilitating pharmacotherapy can include facilitating pharmacotherapy for the subject characterized by melanoma with reduced dose of chemotherapy, epilepsy with reduced dose of antiepileptic drugs, arthritis with reduced dose of anti-inflammatory drugs, chronic pain opioid addiction with reduced dose of detoxification drugs (clonidine, naltrexone), sleep apnea with reduced dose of sleep-inducing drugs, reduced anesthesia during surgery including patients with surgery phobia, hypertension with reduced dose of blood pressure-lowering drugs, or anxiety with reduced dose of anti-anxiety drugs (anxiolytics).

In one aspect, the present disclosure provides a method to facilitate non-pharmacological therapies, the method comprising: delivering to a subject with a stimulator a series of stimuli consisting of both painful and non-painful stimuli, wherein a portion of each of the painful and the non-painful stimuli is delivered during a systolic phase of the subject's cardiac cycle and the remaining portion of each is delivered during a diastolic phase of the subject's cardiac cycle. The method can further comprise repeating one or more times delivering to the subject the series of stimuli, until the non-pharmacological therapies are facilitated for the subject. The method can further comprise repeating one or more times the delivering to the subject the series of stimuli, wherein the painful and the non-painful stimuli are re-determined for the subject prior to the repeating delivery, until the non-pharmacotherapies are facilitated for the subject.

In the method, the non-pharmacotherapies can comprise one of psychological therapies, cognitive behavioral therapy, hypnosis and meditation, acupuncture, trans-cutaneous electrical stimulation, and transcranial magnetic stimulation, physical therapies, massage, manipulation, cardiovascular training, and combinations thereof.

In the method, the stimuli can be delivered to or through an implanted device.

In the method, one or more electrode(s) can be implanted on or near a peripheral or other nerve or the heart system.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

EXAMPLES

Example 1

Cardiac Gating of Peripheral Afferent Stimulation Restores Baroreflex Sensitivity, Reduces Pain Sensitivity and Clinical Pain Report in Fibromyalgia Patients The following study was performed to test certain aspects of the disclosed subject matter on a group of subjects characterized by fibromyalgia and according to specific exclusion requirements. Thus, the description and requirements of the study detailed below in this Example 1 may not apply to all other aspects of the disclosed subject matter.

An important component of intrinsic pain regulatory systems is defined by cardiovascular dynamics that influence baroreceptor sensitivity (BRS). In healthy individuals, an elevation in resting arterial blood pressure is related to reduced pain sensitivity. The present study tested: (1) whether this relationship is altered in fibromyalgia (FM) and (2) whether the introduction of noxious and non-noxious electrical stimuli introduced during systolic and diastolic phases of the cardiac cycle influences perception of experimentally evoked and ongoing clinical pain. Thirty pain-free normotensives (HC) and 32 FM participated in two 8-minutes-trials in which sensory stimuli and stimuli of 50% and 75% of the electrical pain tolerance (SP-protocol) were administered to a finger in randomized order. In control conditions, participants experienced two trials with only painful electrical stimuli (P-protocol), and a trial with both non-painful and painful stimuli independent of cardiac cycle phase (Non-SP-protocol). The magnitude of clinical pain, and of sensory, pain and tolerance thresholds to electrical stimuli were assessed before, between and after the test trials. BRS, blood pressure (BP), heart rate variability (HRV), surface electromyogram, (EMG) and respiration were measured throughout the session. Pain and tolerance thresholds were significantly different between FM and HC, and increased by 15.1% and 25.2% in FM during the SP protocol in contrast to 9.4% and 11.6% for HC. In contrast, the increase in thresholds in FM were significantly lower during both the P- and the Non-SP-Protocol than in HC ($P<0.001$). Clinical pain significantly decreased 20% during the SP-Protocol but not during the P- and Non-SP-Protocols. BRS was diminished in FM compared to HC ($p<0.01$) and correlated with increases in BP and decreases in clinical pain (all p's$<0.01$). Despite the diminished baseline BRS in FM, a combination of painful and non-painful electrical stimuli applied during specific phases of the cardiac cycle diminished pain sensitivity and reduced fibromyalgia pain suggesting an intrinsic operant conditioning of BRS.

Introduction

The 1990 research criteria for fibromyalgia syndrome (FM) characterized this disorder by the presence of widespread pain combined and tenderness at 11 or more of 18 specific 'tender points'. These criteria have been used for clinical diagnosis until the development of recent criteria that include the Widespread Pain Index (WPI) and the Symptom Severity (SS) scale that evaluates symptoms such as fatigue, sleep impairment and different autonomic symptoms (Wolfe et al., 1990, 2011). There is no consensus regarding the mechanisms underlying the set of symptoms reported by FM sufferers.

An emerging body of evidence provides support for an important interaction between pain processing and cardiorespiratory regulatory systems (Bruehl & Chung, 2004; Maixner, 1991; Randich & Maixner, 1984; Maixner et al., 1995). It is generally accepted that the stimulation of carotid sinus and cardiopulmonary baroreceptor afferents, which are activated by dynamic changes in cardiovascular and respiratory parameters, reduce the magnitude of perceived pain. This attenuation of pain is mediated by activation of endogenous pain inhibitory systems, including central nervous system processes that inhibit activity in the ascending reticular activating system (ARAS), a non-specific cortical projecting system. The ARAS plays an important role in sculpting sensory, motor, and autonomic responses to somatosensory input (Steriade 1988, Steriade and Llinas 1988). In healthy individuals, a functional interaction of the cardiovascular and pain regulatory systems has been established whereby elevation in resting arterial blood pressure is related to reduction in pain sensitivity. The activation of carotid sinus and cardiopulmonary afferents through the NTS which activates parasympathetic system and attenuates perceived pain.

Recent studies have also shown that persistent pain conditions may be mediated in part by impairments in this interaction between blood pressure and pain sensitivity (Thieme & Turk, 2006). Diminished baroreceptor sensitivity may have an important impact on pain chronicity (Maixner 1997; Bruehl & Chung, 2004); Bruehl et al., 1998).

The immediate goals of these studies are to determine: 1) if the relationship between cardiac baroreflex sensitivity (BRS) is altered in patients suffering from FM and 2) whether the gating of sensory input in relationship to the cardiac cycle can restore the relationship between baroreceptor sensitivity in a manner that is clinically meaningful in subpopulations of FM patients.

Materials and Methods
Participants

Thirty-two female FM patients recruited at the University of North Carolina from the hospital, pain clinics and rheumatology outpatient departments and 30 age and sex-matched normotensives healthy control subjects (HCs) served as subjects. All patients met the American College of Rheumatology FM criteria (Wolfe et al., 1999, 2011). Sympathetic tone of the patients was significantly higher than the controls. Participants were recruited between May 2010 and December 2012. The exclusion criteria consisted of: hypotension, inflammatory cause of the pain; neurological complications; pregnancy; concomitant severe disease; intake of beta blockers, muscle relaxants and opioids; major psychiatric disorders; and lack of language fluency. An institutional review board approved the study, which adhered to the Declaration of Helsinki and informed consent was obtained from all study participants.

Table 1 shows diagnostic information associated with FM patients and HCs. The sex-matched female HCs and FM patients were comparable with respect to age and demographic state.

Procedure
Clinical Assessment

A physician performed an examination that included laboratory measures (i.e., rheumatoid factor, antinuclear antibodies, erythrocyte sedimentation rate), and the evaluation of tender points (manual tender point survey Okifuji, 2002) on all FM patients. The manual tender point survey was also performed on the HCs.

Psychophysiological Assessment

Patients and HCs were instructed not to consume any analgesic, antidepressant or antihypertensive (e.g., β-blockers) medication for one day prior to their scheduled psychophysiological assessment. A 35 minute psychophysiological protocol was conducted subsequent to the medical and psychological assessments.

Figure 1:
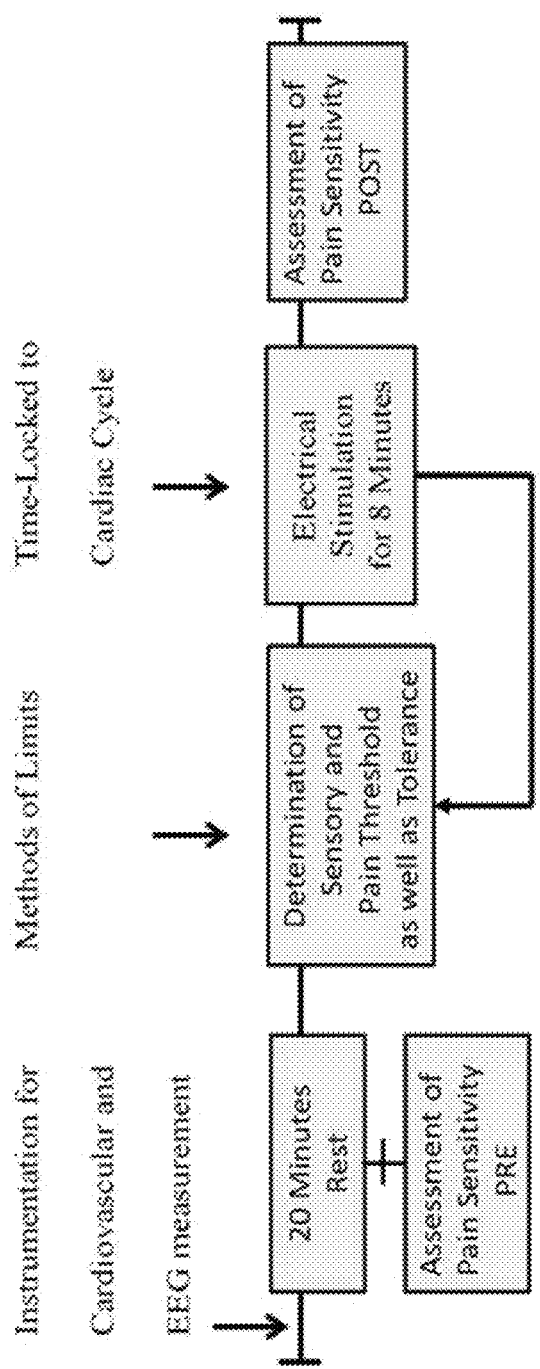
FIG. 1 is a schematic diagram showing the design of the protocol according to one or more embodiments of the present disclosure.

The protocol consisted of seven phases (FIG. 1) with changes of threshold determination and stimulation phases:

Phase I—Baseline threshold determination: The participants received 250 msec trains of electrical stimuli administered to the ring and index finger of the right hand. Each train consisted of 10 individual pulses (7 msec duration with an interpulse interval of 27 msec) delivered over a period of 250 msec. Pulse intensities increased incrementally in 200 µA steps from 200 to a maximum of 10000 µA. The electrical sensory threshold, pain threshold and pain tolerance were determined during each of two trials. After the delivery of each 250 msec pulse train, participants rated their perception of the intensity of electrical test stimulus on an 11 point scale with the verbal anchors of 'no pain' to 'most intense imaginable pain'. The largest electrical stimulus rated as '0' was used to define the electrical sensory threshold, stimuli rated as either '1' or '2' were used to calculate electrical pain threshold, and stimuli rated as '10' were used to define the electrical pain tolerance values. Values obtained from two ascending set of trials were averaged to calculate mean electrical sensory threshold, pain threshold, and pain tolerance values. The individually-determined pain tolerance value was used to calculate the 50% and 75% of pain tolerance values. These values were chosen because studies of operant conditioning in chronic pain showing that pain stimuli higher than 49% of tolerance can trigger operant conditioning of pain inhibition (Flor 2002). These stimuli were used in Phase II of the protocol.

Phase II—The $1^{st}$ trial of the Sensory-Pain (SP)-Protocol: Individually determined sensory (non-painful) and painful (50% and 75% of tolerance value) electrical stimuli (250 msec pulse trains) were administered at a low-frequency of stimulation (0.2 Hz) in a random order during either the systolic or diastolic phase of the cardiac cycle for 8 minutes. This resulted in the delivery of a total of 66 electrical stimuli during an 8 minute period, 22 for each value (i.e., sensory threshold, 50% and 75% of electrical tolerance values). Half of the stimuli for a given parameter (i.e., sensory threshold, 50% and 75% of electrical tolerance values) were administered during the systolic phase of the cardiac cycle and an equal number (11 for each parameter) were administered during the diastolic phase of the cardiac cycle.

Phase III—Threshold determination 2: The participant received electrical stimuli in an ascending order twice (200 µA-4600 µA) and were asked to rate the stimulus-evoked sensations up to individual pain tolerance using the same protocol as described for Phase I of the protocol. When changes of the thresholds were observed, values of the 3 individual test stimuli were recalculated.

Phase IV—The $2^{nd}$ trial of SP-Protocol: The recalculated sensory, 50%- and 75%-stimuli of the individual pain tolerance were delivered for 8 minutes.

Phase V—Threshold determination 3: The ascending trains of electrical stimuli were again delivered twice, the sensory and pain threshold as well as pain tolerance were determined and the test stimuli were recalculated dependent on the individual pain tolerance.

Phase VI—The $3^{rd}$ trial of SP-Protocol: The recalculated sensory, 50%- and 75%-stimuli of the individual pain tolerance were delivered for 8 minutes.

Phase VII—Post-Threshold determination 4: The ascending trains of electrical stimuli were again delivered twice, the sensory and pain threshold as well as pain tolerance were determined and defined as post-values.

Control Conditions.

In control condition 1, participants experienced two 8-minutes trials with only painful electrical stimuli (P-protocol) delivered immediately after the systolic peak. The control condition using only painful stimuli tests the influence of associative and classical conditioning of pain inhibition, especially.

In control condition 2, individual non-painful sensory and test stimuli at 50% and 75% of the tolerance threshold were delivered independently of the cardiac cycle in two 8-minute-trials (Non-SP-protocol). The application of non-painful and painful stimuli independent of cardiac cycle was considered to be a placebo condition.

Sensory, pain and tolerance thresholds to electrical stimuli as well as clinical pain ratings were assessed before, between and after the test trials given in each protocol. Blood pressure (BP), BRS, and evoked potentials were measured throughout the session.

Psychophysiological Recordings

Participants were seated and positioned in a straight back chair and were instructed to move as little as possible. All instructions were presented on a video screen.

Electromyogram (EMG) activity was recorded from the right m. trapezius according to the positioning recommended by Fridlund and Cacioppo (1986). BP was continuously monitored using an Ohmeda Finapres BP monitor (Datex-Ohmeda, Louisville, Colo., USA). A LabLinc V modular instrument series (Coulbourn Instruments, USA) was used to record EMG, skin conductance level (SCL), and electrocardiogram (ECG).

The presentation of the instructions, data acquisition, and data storage were computer-controlled. The sampling frequency of EMG signals was 3,000 Hz. The raw EMG was amplified by a factor of 100,000, passed through a bandpass filter (25 to 1,000 Hz), and integrated using contour-following integrators with a time constant of 70 ms.

BP was measured with a photoplethysmographic device on the fourth digit of the left hand (the accuracy of this procedure is ±2 mmHg±0.25 kPa). A computer program that summed the digitized beat-by-beat waveforms averaged the sample time synchronized to the R-wave of the electrocardiogram, and divided them by the number of cardiac cycles. Heart rate (HR) in beats per minute (Jennings et a., 19981) was determined by photoplethysmography of HR waveforms positioned on the tip of the fourth digit of the right hand. BRS was calculated as the ratio of BP and HR (Watkinson et al., 1996). SCL was measured through two electrodes in a sensor with a surface of 50.3 mm2 on the second digit of the right hand about a constant current procedure of 4 µA (Boucsein, 1988). Respiration rate (RR) was assessed by impedance pneumography (Q-Rip-Sensor).

Heart rate variability (HRV) was evaluated by both ECG and beat-to-beat changes in blood pressure using the program described by Berntson et al. (1997), see the recommendations provided by the task Force of the European Society of Cardiology and the North American Society of Pacing and Electrophysiology. For time domain measures, SDNN (standard deviation of normal-to normal [N-N] interval) and RMSSD (root mean square of the differences between successive N-N interval) provided estimates of high-frequency variations in HR in short term recordings that reflect parasympathetic regulation of the heart.

In addition, standard measures in the frequency domain included total power (TP) reflecting overall autonomic activity, very low frequency (VLF) as an indicator of activity of slow temporal processes regulated by sympathetic nervous system, low frequency (LF) as a strong indicator of sympathetic activity in long-term recordings, and high frequency (HF) reflecting parasympathetic activity.

All Physiological Measurements were Recorded Continuously.

Systole-Stimulus-Synchronizer.

Figure 2:
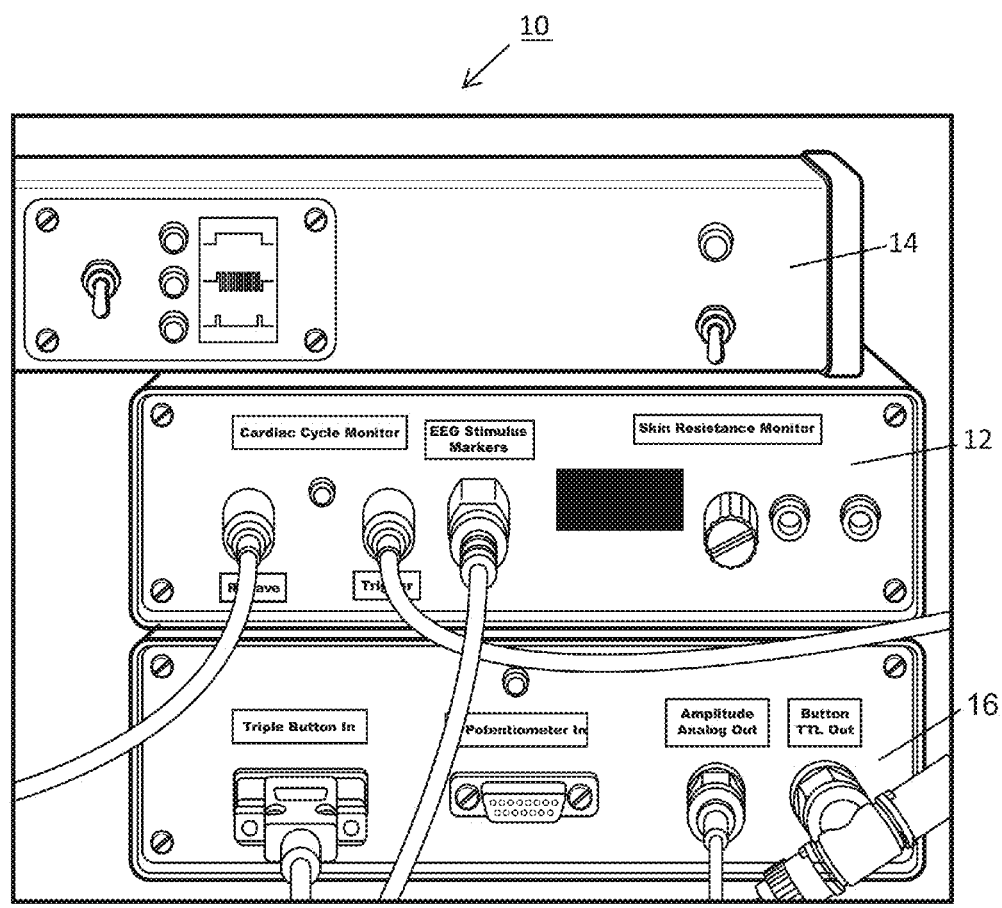
FIG. 2 is a view from the back of a Systole Stimulus Synchronizer device according to one or more embodiments of the present disclosure.

To enable the delivery of 250 msec electrical pulse trains that were phase locked to either the systolic or diastolic phases of the cardiac cycle, a device was fabricated that assessed the R-wave from a 3-lead ECG signal on a beat-by-beat basis. This device, the Synchronizer, was used to trigger a constant current electrical stimulator (Coulbourn Instruments A13-75 Bioelectric Stimulus Isolator) which delivered electrical pulses during specified periods of the cardiac cycle (see FIG. 2). In order to determine the cardiac phase, consecutive inter-beat-intervals were used to dynamically calculate an average inter-beat-interval from 3 inter-beat-intervals. This value was used to present the electrical test stimulus during the next beat within a specified percentage of the cardiac cycle calculated from 3 previous inter-beat-intervals. The 250 msec pulse trains delivered during the systolic phase were delivered at the 20% value of the average inter-beat-interval. Diastolic associated pulse trains were delivered at the 80% value of the dynamically determined average inter-beat-interval.

The Synchronizer is used to deliver electrical stimuli before and after the systolic peak—relevant for the activation of the pain inhibition system.

Data Analysis

Data analyses were performed in sequential steps. The first analyses examined baseline differences in sensory and pain thresholds as well as tolerance in the FM and HC groups after outlier elimination defined greater than 2 sigma. Repeated measures analyses of covariance (ANCOVAs) effects depending on baseline differences with all three phases of threshold determinations as a within factor and the two groups as between factors in SP-, P- and Non-SP-protocols were followed by post hoc t tests. These post hoc analyses were used to calculate: (1) group differences over all three phases of threshold determination in each protocol; (2) group differences in percentage change of pain thresholds and tolerance in each protocol. To assess the efficacy of the protocols for increasing thresholds, the pain and tolerance thresholds after the $2^{nd}$ trial were compared for each group using paired-sample t-tests. The second step assessed changes in clinical pain before and after each protocol. The $3^{rd}$ step assessed BL differences of BRS using t-tests for within and between group comparisons. The $4^{th}$ step measured the natural log HRV variables (TP, HF, LF, VLF, SDNN, RMSDD) in FM and HC and tested changes in each protocol using non-parametric tests for between (U-test) and within group comparisons (Friedman-Test) because of non-normal data distributions. Further, the changes between baseline and each trial were compared between the different protocols. The $5^{th}$ step calculated changes of clinical pain, pain threshold and pain tolerance as well as BRS before and after pain treatment by operant behavioral treatment (OBT) combined with provision of the SP-protocol.

Results

A. Thresholds

Baseline of Sensory, Pain and Tolerance Thresholds.

Figure 3:
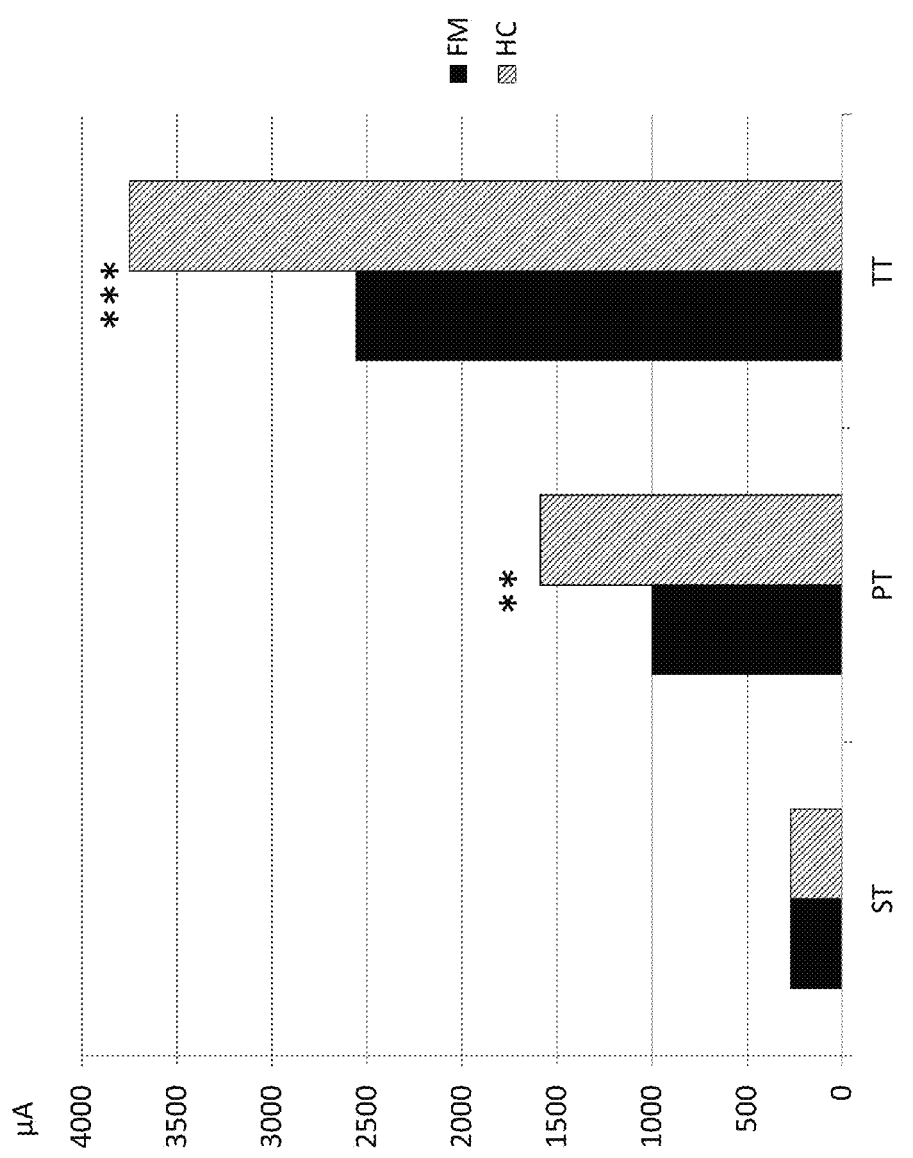
FIG. 3 is a bar graph showing baseline thresholds to electrical stimulation according to one or more embodiments of the present disclosure. Sensory thresholds (ST), pain thresholds (PT) and pain tolerance thresholds (TT) are shown for fibromyalgia patients (FM) by solid bars and for healthy control subjects (HC) by diagonal stippled bars. The differences in pain and tolerance thresholds between FM and HC were significant for pain threshold,  $p<0.01$ and for pain tolerance threshold * $p<0.001$.

In contrast to comparable sensory thresholds (ST) in FM patients and HC, pain threshold (PT) (F(1;69)=20.36, p<0.001) and tolerance (TT) (F(1;69)=28.75, p<0.001) values were significantly different. FM patients showed a 12.89% lower pain threshold (PT) and a 25.85% lower tolerance (TT) than HC's (FIG. 3).

Changes of Thresholds in Different Protocols.

In the SP-Protocol, the ANCOVA showed a significant threshold×trial×group×interaction for sensory and pain thresholds as well as for tolerance (F(4;107.88)=3.056, p=0.018) with significant differences between FM and HC (p=0.008). In FM, pain threshold (PT) and tolerance (TT) increased 15.1% and 25.1% (both p's<0.001) in contrast to HC showing increases of 9.4% and 11.6%, respectively (both p's<0.01, FIGS. 4A-4B). After two 8-minute stimulations following the SP-Protocol, pain threshold and tolerance values in FM was significantly higher than these values assessed after the P- and Non-SP-Protocols (all p's<0.05).

For the P-Protocol, a significant threshold×trial×interaction (F(2;145.85)=7.65, p=0.001) was found that differed between groups (p=0.045). In contrast to the SP-Protocol, HC increased their pain (9.38%) and tolerance (14.95%, p=0.006) thresholds to a greater degree than FM, which showed a PT increase of 6.88% and TT increase of 9.95% (p=0.042, FIGS. 4A-4B).

Figures 4A, 4B:
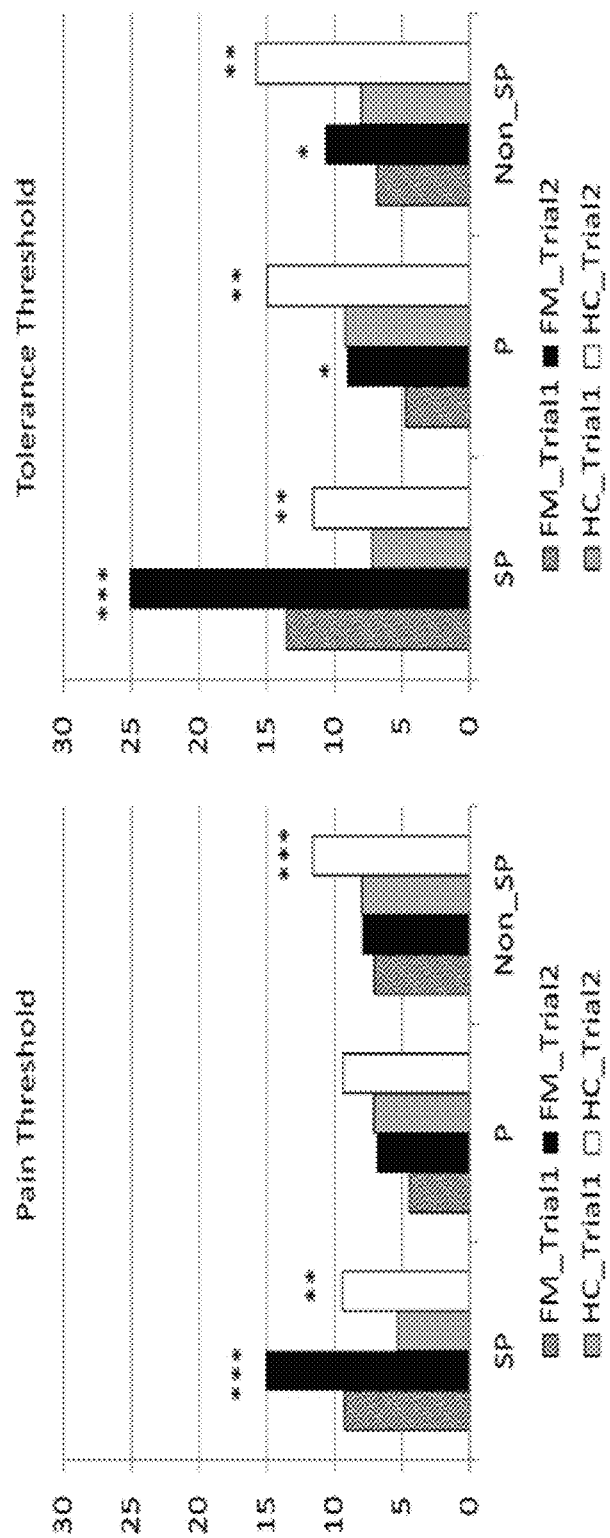
FIGS. 4A-4B are bar graphs showing pain thresholds and tolerance thresholds increased after each protocol in each trial, indicating reduced pain sensitivity to the electrical stimulation according to one or more embodiments of the present disclosure. The Y axis shows percentage increase of pain thresholds in graph (A) and percentage increase in tolerance thresholds in graph (B). Results for each of the SP-, P- and Non-SP stimulation protocols are grouped separately. Within each group the increase for fibromyalgia patients (FM) are shown on the left and the increase for healthy control subjects (HC) is shown on the right. The increases in trial 2 were greater than those in trial 1 for all protocols. The largest increases were observed in fibromyalgia patients for both pain threshold and pain tolerance, * $P<0.05$,  $p<0.01$ * $p<0.001$.

The Non-SP-Protocol displayed a significant threshold× trial×interaction (F(2;165.83)=8.67, p=0.001) in which the groups differed as a trend (p=0.065) and HC showed greater increase in pain threshold (PT) and tolerance (TT) than FM (FIGS. 4A-4B).

Efficacy of Protocols for Increasing Thresholds.

Pain threshold and tolerance in FM patients assessed after the SP-Protocol were significantly higher than pain threshold and tolerance after the P-Protocol (PT: t(31)=2.675, p=0.021, TT: t(31)=2.476, p=0.028) and Non-SP-Protocol (PT: t(31)=3.175, p=0.041, TT: t(31)=3.174, p=0.006). For HC, the effects of the SP-Protocol on pain threshold and tolerance were not significantly different from the effects of either the P- or Non-SP-Protocol.

B. Changes of Clinical Pain

Figure 5:
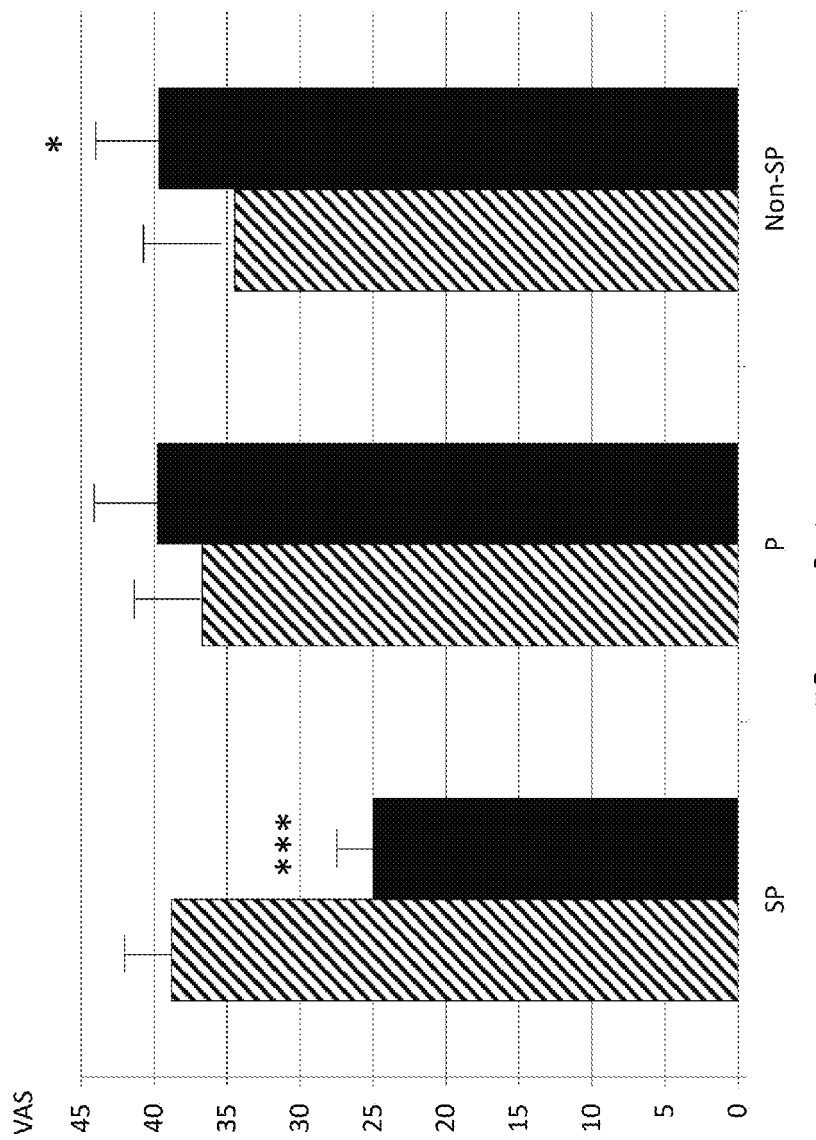
FIG. 5 is a bar graph showing visual analog scale (VAS) ratings of pain magnitude before and after each type of stimulation protocol in patients with fibromyalgia according to one or more embodiments of the present disclosure. Each protocol was administered in two 8-minute trials and the figures shows ratings before the first trial (Pre) and after the second trial (Post). Pain ratings decreased significantly after the SP-Protocol and increased slightly after the control P- and Non-SP-Protocols, * $P<0.05$, *** $P<0.001$.

The mean visual analog scale (VAS 0-100) rating of clinical pain in FM patients prior to stimulation was 40 on the 100 point VAS. ANCOVA showed a significant protocol×time interaction (F(2;53)=11.92, p<0.001): In FM patients, the SP-Protocol resulted in a significant reduction in clinical pain by 17.05% (t (31)=3.825, p=0.001) after two 8-minute stimulations, the P-Protocol did not show any significant differences, and the Non-SP-Protocol showed a significant increase reported clinical pain (t (31)=-2.105, p=0.042) (FIG. 5).

C. Changes in BRS

Due to the lack of synchrony between blood pressure and heart rate essential for the calculation of BRS, these values could be calculated for only 51.53% of FM and 53.89% of HC. The reduced sample was sufficient for (1) independent sample t-tests of the differences between FM and HC, as well as for (2) paired-sample t-tests to determine which protocol showed the most significant change in BRS.

Figure 6:
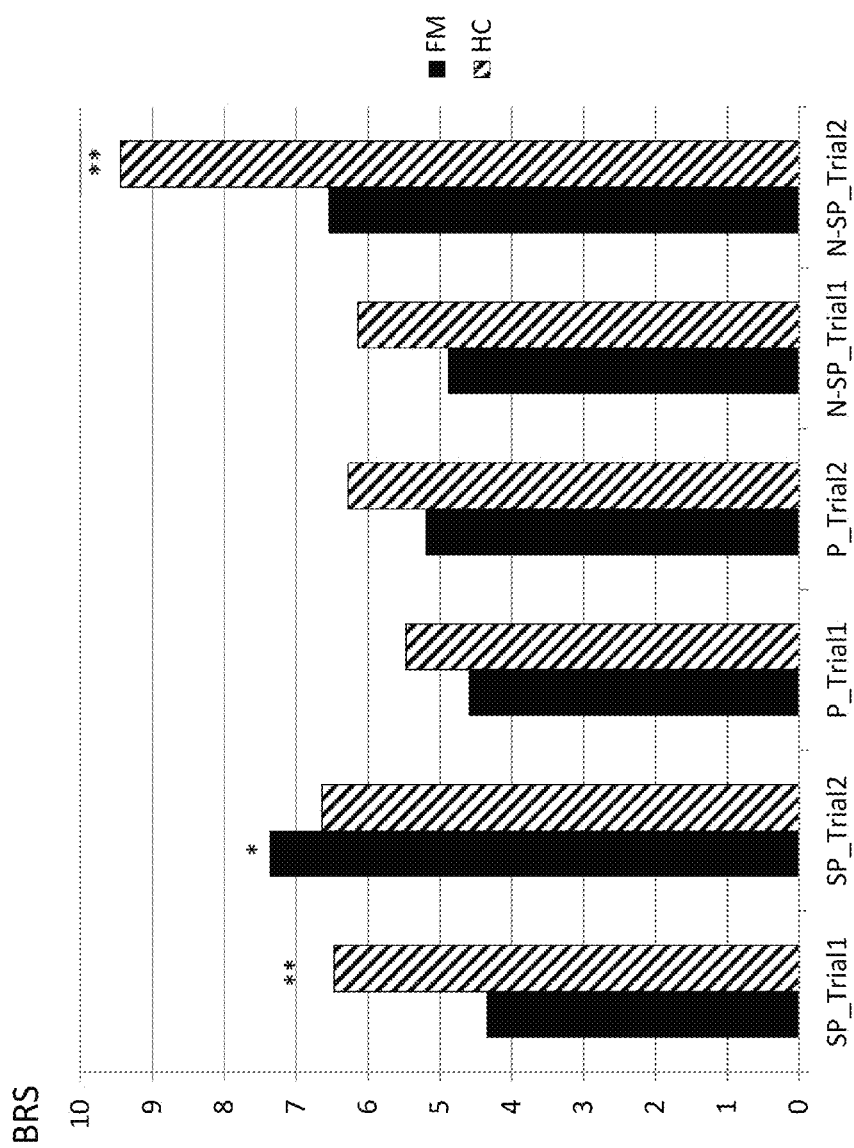
FIG. 6 is bar graph showing mean baroreflex sensitivity (BRS) values (ms/mmHg) obtained following Trials 1 and 2 for fibromyalgia (FM) and healthy control (HC) subjects in response to the SP-, P- and Non-SP-protocols according to one or more embodiments of the present disclosure. * $P<0.05$, ** $p<0.01$ comparing FM to HC.

FM patients showed significantly lower BRS than HC in both trials of the SP-Protocol (p=0.009, p=0.007) and the P-Protocol (p=0.023, p=0.022), but no significant differences in the Non-SP-Protocol (FIG. 6).

Figure 7:
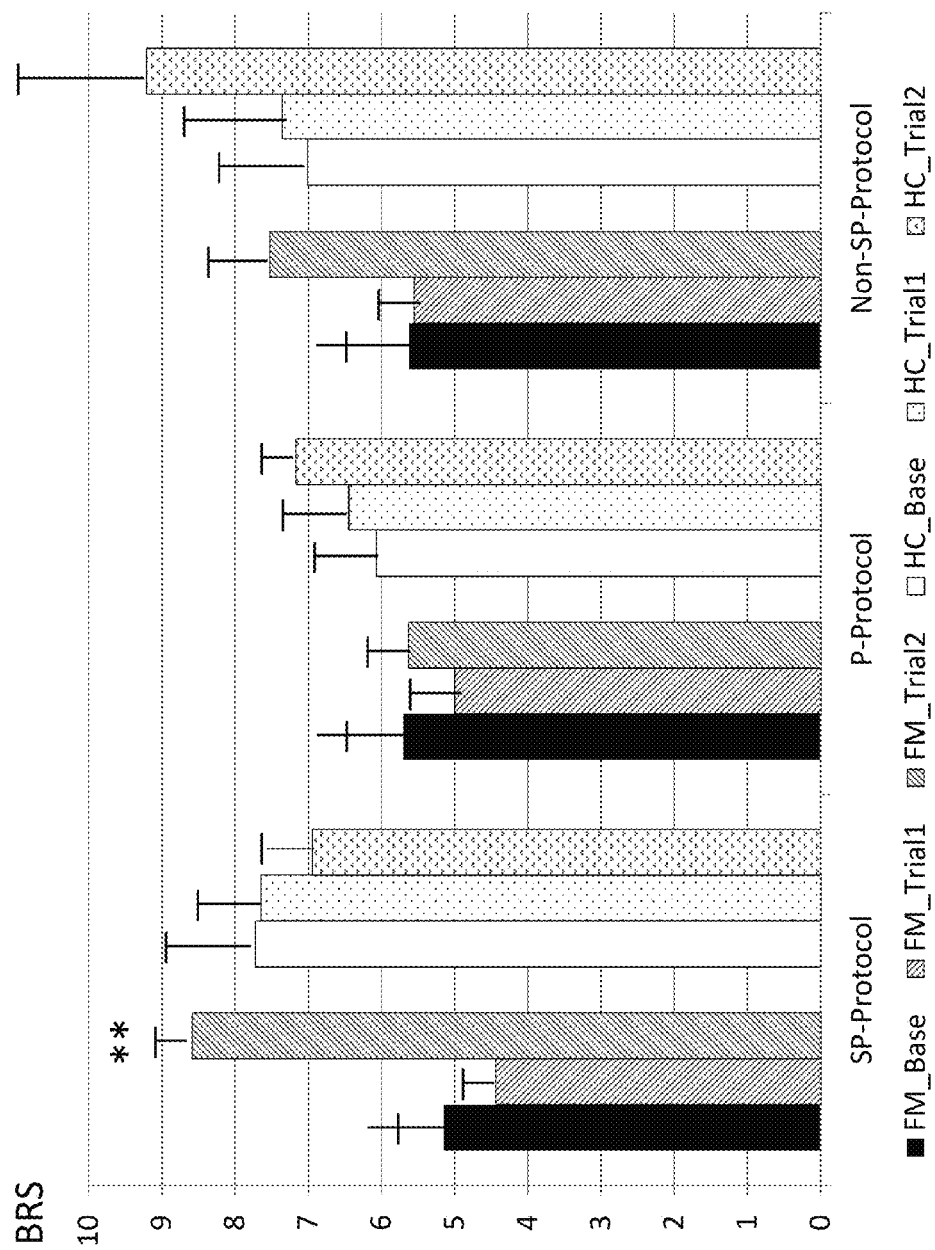
FIG. 7 is bar graph showing progression of changes in mean baroreceptor sensitivity over stimulation trials according to one or more embodiments of the present disclosure. Mean baroreflex sensitivity (BRS) values (ms/mmHg) are shown separately for the SP-, P- and Non-SP-Protocols. Within each group of six histogram bars, BRS values for fibromyalgia patients (FM) are shown on the left and BRS values for healthy control (HC) subjects are shown on the right. The three adjacent histogram bars shown BRS before the two trials, after the first trial, and after the second trial. BRS increased significantly, ** $p<0.01$, over the SP-Protocol trials in patients with fibromyalgia compared to Baseline.

The SP-Protocol displayed significantly increased BRS between baseline and the $2^{nd}$ trial (t(15)=3.17, p=0.012) as well as between the $1^{st}$ and the $2^{nd}$ trials (t(15)=3.163, p=0.019) and the $1^{st}$ and $3^{rd}$ trials (t(15)=2.53, p=0.028) in FM but not in the P- and Non-SP-Protocols. For HC, significant changes of BRS were found between the $1^{st}$ and $2^{nd}$ trials of Non-SP-Protocol (t(17)=4.53, p=0.008) but not during SP- and P-Protocols (FIG. 7).

D. Baseline and Changes in HRV

Figure 8:
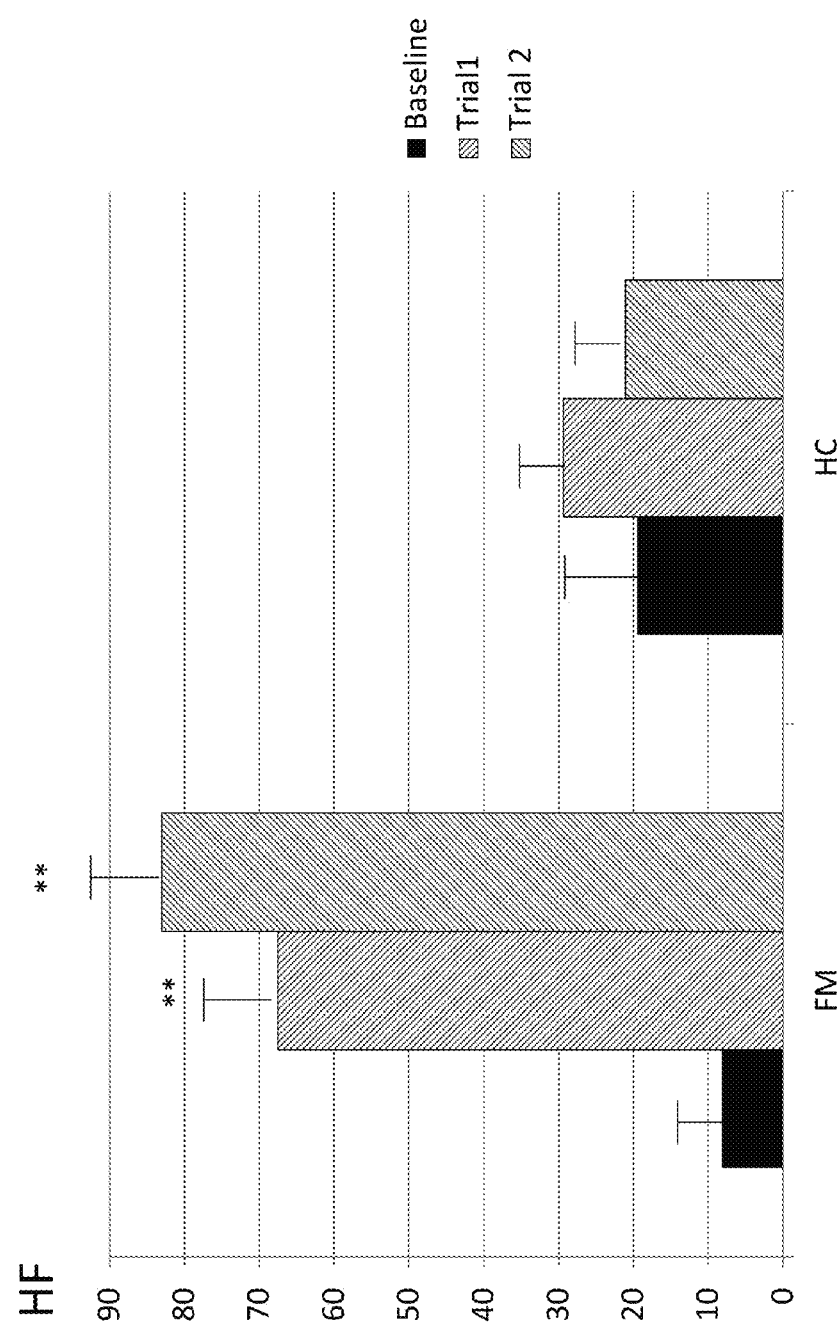
FIG. 8 is a bar graph showing progression of changes in vagal activity measured at high frequency (HF) over stimulation trials in the SP-Protocol according to one or more embodiments of the present disclosure. Vagal activity before the first trial and after the first and second trials are shown for fibromyalgia patients (FM) on the left and for healthy control (HC) subjects on the right. Vagal activity in fibromyalgia patients was significantly greater after each trial ** $p<0.01$.

The baseline of different HRV variables such as TP, HF, LF, VLF, SSDN, RMSSD was significantly lower in FM patients in comparison to HCs (all p's<0.003, table 2 and FIG. 8).

In contrast, only 6 of 36 HRV variables collected during the SP-, P- and Non-SP-protocols were significantly different between FM patients and HCs: TP during the trial $1^{st}$ of the P-protocol (p=0.021), LF during the $1^{st}$ trial of Non-SP-protocol (p=0.037), VLF of the $1^{st}$ and $2^{nd}$ trial of the SP-protocol (both p<0.05), and RMSSD during the $2^{nd}$ trial of the Non-SP-protocol (table 2 and FIG. 8).

Within group differences showed that FM patients exhibit a significant increase from baseline values across trials for most HRV variables (all p<0.015) except for VLF during the Non-SP-protocol, which contrasts with HCs who did not show significant changes in HRV values between baseline and treatment trials (table 2 and FIG. 8). Considering the changes in HRV measures across trials relative to baseline values in FM participants, the change in HF was significantly greater between SP- and the other treatment protocols, (both p's<0.01), LF and VLF changes were significantly lower (all p's 21 0.03) in the SP-protocol compared to the control protocols (FIG. 8).

E. Changes in Clinical Pain, Pain Threshold, Pain Tolerance and BRS after Operant-Behavioral Therapy (OBT) and Delivery of the SP-Protocol The decrease of clinical pain, the increase of pain threshold, pain tolerance and BRS after SP-protocol associated with brain inhibitory systems might be based on the activation of brain regions involved in descending pain facilitation such as the PAG (Berrino 2001), the NRM (Wiertelak 1997), the NTS (Wiertelak 1997), and the RVM (Pertovaara 1998) that cause a persistent decrease in the sympathetic tone. An association of BRS and brain stem activity within NTS and NRM relevant for pain inhibition was hypothesized and evaluated as described herein, and termed the SP-protocol. The SP-protocol was further evaluated as a component of a new treatment method.

The SP-protocol was combined with operant behavioral therapy (OBT). OBT was chosen because it is currently the most effective treatment in FM with 65% responder rate in an inpatient and 58% responder rate in an outpatient setting with a pain reduction of 50%, at least, measured 12 months after OBT (Thieme et al. 2003, 2006, 2007).

Treatment

Each treatment consisted of 5 weekly, 2×2-hour sessions co-led by a psychologist and rheumatologist and was conducted as a single therapy. Spouses attended 5/10 sessions: the first, third, fifth, seventh, and tenth session. OBT was based on a structured manual (Flor, Birbaumer, 1994; Thieme et al., 2006). Each treatment session started with an hourly session of the OBT program followed by an hourly SP-protocol session.

Operant-Behavior Therapy

The OBT was directed toward changing observable pain behaviors and included video feedback of expressions of pain, contingent positive reinforcement of pain-incompatible behaviors, and punishment of pain behaviors within a group setting. Time-contingent physical exercises were provided according to operant principles (Vlaeyen, 1995) in the sessions and as homework exercises. Patients engaged in role-playing to reduce pain behaviors and increase healthy behaviors. Patients were encouraged to increase their activity levels and were assigned homework that included specific instructions to increase activities and reduce pain behaviors. A reduction of medication was based on a physician-coordinated individual time-contingent interval plan. In contrast to CBT, this treatment focused primarily on behavioral expressions of pain and emphasized changing inappropriate pain behaviors without directly targeting maladaptive thoughts or cognitive coping.

Material and Methods

Sample

A sample of 40 consecutive married female patients with FM was recruited from 3 outpatient rheumatological clinics. The groups were comparable with respect to demographic and FMS-specific variables (for example, number of TPs and severity of TP pain (Okifuji et al., 2002; Table 1).

Treatment Protocol

Figure 9:
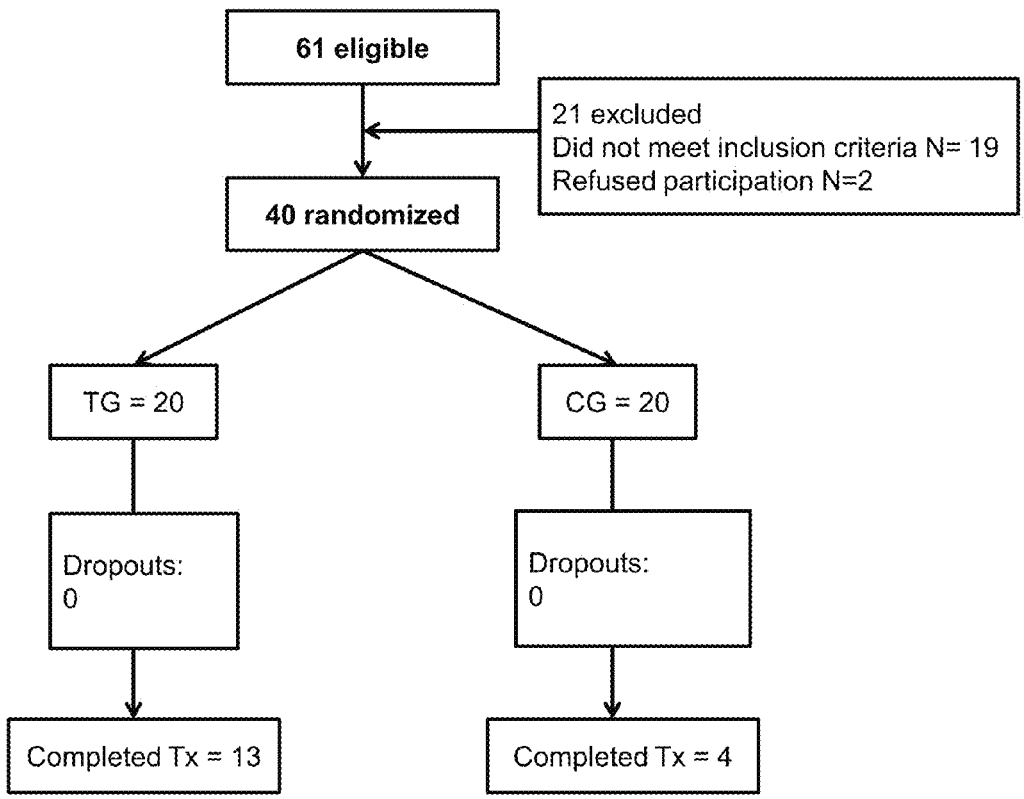
FIG. 9 is a schematic diagram showing consort (Consolidated Standards for Reporting of Trials) diagram for the treatment group (TG) after active treatment and the control group (CG) after placebo treatment according to one or more embodiments of the present disclosure.

All patients signed informed consent and were randomly assigned to either OBT with the SP-Protocol as a treatment group (TG) or to OBT combined with a placebo condition (Non-SP-Protocol) as a control group (CG). The randomized control study was approved by the local ethics committee. Administration of the two types of treatment was counterbalanced to control for time of year and time of entry into the clinical trial. FIG. 9 provides an overview of the patient flow in the study based on the CONSORT guidelines (Moher et al., 2001).

All patients received a general medical and a rheumatological assessment (see below). The inclusion criteria consisted of (a) meeting ACR (American College of Rheumatology) criteria of FM (Wolfe 1999, 2011), (b) pain for a period of at least 6 months, (c) married or significant others, (d) willingness of the spouse to participate, and (e) ability to complete the questionnaires and understand the treatment components. f) Since normotensive individuals reply to an activation of BRS with analgesia (Rau and Elbert 2001), only FM patients with high cardiovascular stress reactivity (Thieme & Turk, 2006) were included. The exclusion criteria consisted of inflammatory rheumatologic diseases and any concurrent major disease such as cancer, diabetes, or kidney failure as well as low cardiovascular stress reactivity as well as mayor psychiatric disorders including personality disorders.

Comorbidities in the patients included: osteoarthritis (84.6%), migraine (22%), restless legs syndrome (15.38%), sleep apnea (30.76%), and PTSD (30.76%).

Treatment Outcomes

At present, 13 patients have been treated with OBT and the SP-Protocol (TG), 11 Patients with OBT and Placebo and 7 patients have not yet finished the therapy (CG). Thus, results are reported for the patients who completed OBT and the SP-Protocol; 7 patients with data at 6 months and 6 patients with data at 12 months follow-up.

Treatment Duration and Number:

While the recent studies (Diers 2012; Flor & Birbaumer, 1994; Thieme et al., 2003, 2006, 2007) needed 30 OBT treatment hours, the protocol reduced the OBT-dose by 66.6% to 10 OBT treatment hours with the entire treatment consisting of 20 treatment hours (10 hr OBT, 10 hr SP-Protocol), which is 33.3% less than needed by current treatment protocols.

Attrition.

None of the 13 treated patients terminated the treatment prematurely.

Treatment Expectation and Satisfaction.

Expectation (t(12)=4.38, p=0.001) and satisfaction after the treatment (t(12)=4.28, p=0.001) were significantly higher than before the treatment.

The rate of adherence of patients was excellent. Only 2.3% sessions were missed and 5.5% of the homework was not completed.

Clinical Significant Improvement of Clinical Pain.

Figure 10:
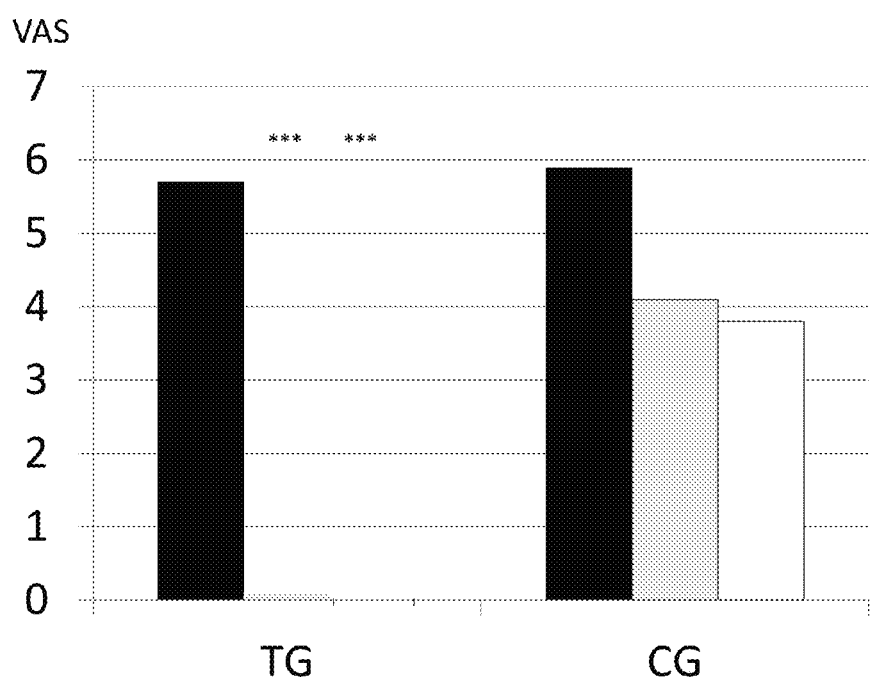
FIG. 10 is a bar graph showing clinical pain ratings using a visual analog scale (VAS) before (black bars), six months after (grey bars), and twelve months after (white bars) operant behavioral treatment (OBT) combined with either active treatment (TG) or placebo treatment (CG) according to one or more embodiments of the present disclosure. Active treatment reduced clinical pain ratings to near zero after 6 months and abolished clinical pain by 12 months, *** $p<0.001$.

Before treatment, the mean pain rating was 44.58 (range 20-85) assessed on a VAS (0-100). At the $10^{th}$ treatment session of OBT combined with the SP-Protocol, all (100%) of the FM patients reported a complete absence of clinical pain (t(12)=34.23, p<0.001), which remained at this level for 6-12 months post treatment (FIG. 10).

Since the study is still in process, the mean values of clinical pain in the CG (N=4) are presented without any calculations of statistical significance.

Three of 13 patients were pain free after the $3^{rd}$ session, 4 patients after the $4^{th}$ session, 4 patients after the $6^{th}$ session and 2 patients after the $8^{th}$ session. Two sessions after reaching a pain free state immediately after the treatment session, the patients reported a longer lasting pain free state for 10 hours that, after completion of all sessions, extended to a pain free state long lasting for 6-12 months. Two patients (15.38%) needed an additional treatment session 3 and 4 months after finishing the treatment due to a painful medical appointment (mammography) and a loss of a significant other. In each case, only 1 treatment session was necessary to return each patient to a pain free state.

Changes in Pain Threshold and Tolerance

Immediately after 10 treatment sessions, pain threshold was significantly increased by 51.45% (t(12)=42.67, p<0.001) and by 50.01% in the 6 and 12 months follow-up (t(12)=40.18, p<0.001). Pain tolerance increased significantly by 113.04% (t(12)=46.12, p<0.001) after 10 sessions treated by OBT and the SP-Protocol and by 111.37% (t(12)=44.89, p<0.001) in the 6-12 months follow-ups.

Increase in BRS

Figure 11:
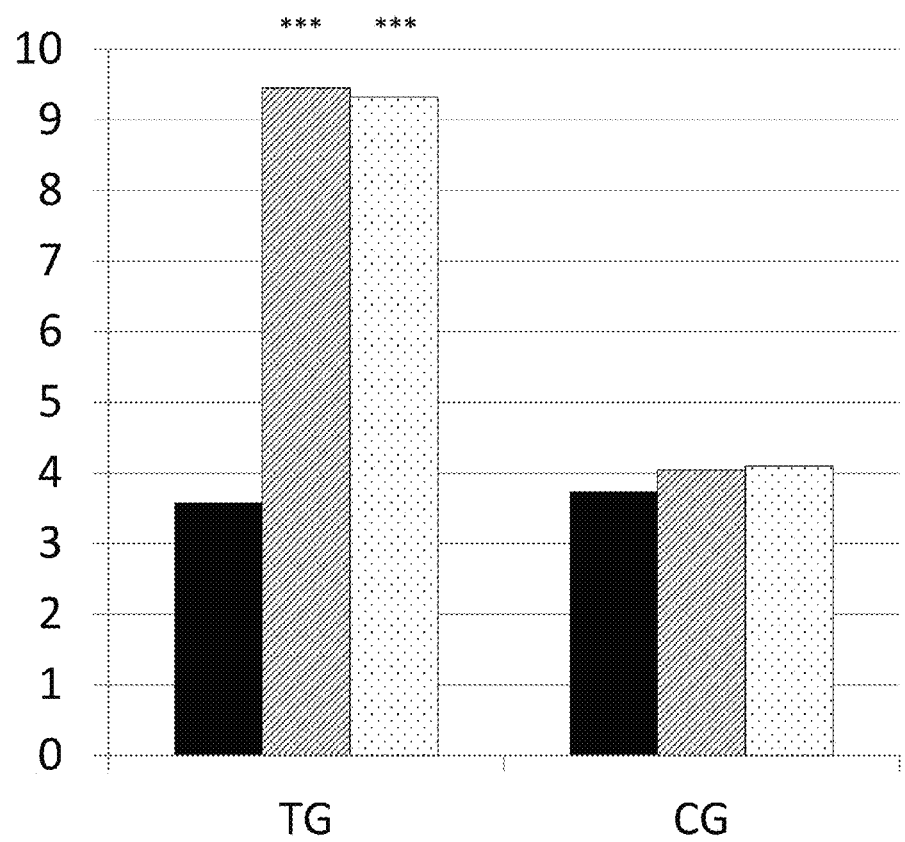
FIG. 11 is a bar graph showing changes of baroreflex sensitivity (BRS) before (black bars), six months after (hatched diagonal line bars), and twelve months after (dotted bars) operant behavioral treatment (OBT) combined with either active treatment (treatment group "TG") or placebo treatment (control group "CG") according to one or more embodiments of the present disclosure. BRS was elevated significantly after 6 months of active treatment and remained elevated after 12 months of active treatment, *** $p<0.001$.

The mean value of BRS before treatment was significantly lower in FM than in HC. FIG. 11 is a bar graph showing changes of baroreflex sensitivity (BRS) before (black bars), six months after (hatched diagonal line bars), and twelve months after (dotted bars) operant behavioral treatment (OBT) combined with either active treatment SP-Protocol (treatment group "TG") or placebo treatment Non-SP-Protocol (control group "CG"). After 10 treatment sessions, the BRS increased significantly (t(12)=18.72, p<0.001) as shown in FIG. 11.

Since the study is still in process, the mean values of BRS in CG (N=4) are presented without accompanying significance.

Comorbidity

Osteoarthritis (OA).

The patients could discriminate between FM pain and OA pain. In contrast to 100% relief of FM pain, OA pain was abolished in 63.6% of the patients. The other patients (36.7%) reduced their OA pain by 43%, reporting a mean clinical pain of 8 assessed by a VAS of 0-100.

Migraine.

The three patients who suffered for 36 years from migraine reported 72 migraine attacks in 6 months (August- January) before the treatment. Every attack lasted 2 days despite intake of Triptane. After treatment, they reported only 3 attacks with a duration of a half day without any intake of Triptane at the comparable time and duration of the year. Further, the patients reported an absence of fatigue and apathy experienced previously after intake of Triptane.

Hypertension.

Before treatment, FM patients showed a mean resting BP of 142/89 and a mean stress reactivity BP of 162/96. After 10 sessions OBT with the SP-Protocol, the mean resting BP was significantly decreased to 118/71 (t(12)=24.69, p=0.014). The stress reactivity BP was significantly decreased to 132/82 (t(12)=32.22, p=0.001).

Sleep Apnea.

The patients (N=4) reported 49.5 apnea episodes during the night measured by a sleep lab before treatment, and no episodes after the treatment. Thus, they could discontinue use of the assisted respiration sleep mask.

Restless Legs Syndrome (RLS).

The diagnosis was made by the department of neurology. After the treatment, the RLS diagnosis was retracted.

Posttraumatic Stress Disorder (PTSD).

The diagnosis was made by a licensed behavioral psychotherapist with 23 years professional experience who used the structured clinical interview for psychiatric disorders (SCID). After the treatment, the PTSD and the symptoms of increased physical arousal, intrusions, emotional numbness were absent.

Further treatment studies that show additional claims for the treatment.

$1^{st}$ Study with Exam Phobia.

Medical students are often very affected by exam phobia. Usually, 12 sessions of systematic desensitization (SD) combined with relaxation (autogenic training) is sufficient, with high effect sizes. The combination of SD with the SP-Protocol reduced the dose from 12 to 2 sessions in four patients. All of them passed their exams and showed an effect maintained for at least 3 months.

$2^{nd}$ Study with Rheumatoid Arthritis (RA).

Four patients reported a higher clinical pain (VAS=55.2) than usually reported by RA patients. All four patients were taking a combination of MTX therapy and high doses of cortisone (>7.5 mg) as well as and 14 inflammatory episodes of RA in 6 months, before the treatment. After the treatment, pain was reduced to VAS=14.6, and they experienced only 2 inflammatory episodes. Rheumatologists reported lower CRP and BSG values after treatment.

Discussion

The goal of this study was the development of a protocol useful for the evaluation and increase of baroreflex sensitivity and sympathetic parasympathetic balance in chronic pain patients with the goal of reducing chronic pain.

Validity of Experimental Manipulation.

The significant increase of BRS associated with an increase of pain threshold and tolerance after the two 8-minutes stimulation with pain- and pain-free electrical stimuli after systolic peak as compared to the baseline and the control conditions demonstrates that clinical pain was successfully inhibited by the SP-protocol.

Threshold Data.

Before the stimulation, pain threshold was 12.89% and tolerance 25.85% significantly lower in FM patients than in healthy individuals. These results are comparable to previous studies using electrical (e.g. Banic, 2004), mechanical (e.g. Gracely, 2002), and thermal (e.g. Staud 2004) pain stimuli associated with temporal summation and wind-up (e.g. Graven-Nielsen, 2000, Staud 2004) and secondary hyperalgesia and central sensitisation (e.g. Burgmer 2012, Woolf 2011). Neuroimaging studies show the decreased pain threshold and tolerance is related to cortical or subcortical augmentation of pain processing (Gracely, 2002) and might be related to changes in cerebral-midbrain-spinal mechanisms of pain inhibition (Burgmer 2012).

After the stimulation with pain and pain-free stimuli after SP-protocol, pain threshold and tolerance in FM patients were increased by 15.1% and 25.2%, respectively, whereas healthy individuals increased their pain threshold and tolerance by 9.4% and 11.6%. In contrast, when FM patients received only painful stimuli delivered only after the systolic peak (P-protocol), the pain threshold and tolerance were not increased. The combination of pain with pain-free stimuli likely provokes associative learning known as classical conditioning that is comparable to the behavioural therapy of anxiety disorders, which combines noxious and relaxation stimuli resulting in an anxiety-free state. Recently published studies show changes in the prefrontal cortex related to classical conditioning (Kircher, 2012). Early studies in patients with chronic pain showed an influence of classical conditioning on pain chronicity. Flor and colleagues (1994a) showed that recalling a recent stress or a recent pain episode was associated with an increase in muscle tensions in low back pain patients, an important component of the pathogenesis of this disease. Jensen and colleagues (2012) showed that changes of maladaptive pain cognitions by CBT treatment was related to changes in activity in brain areas such as PAG, insula and ACC. Differences in brain responses between electrical stimulation with and without classical conditioning of pain stimuli after systolic peak are obvious targets of future studies.

In the $2^{nd}$ control condition, painful and non-painful stimuli were applied independently of cardiac cycle (Non-SP-protocol). In contrast to the SP-protocol, pain threshold and pain tolerance were not increased in FM in the Non-SP protocol. Only the SP-protocol increased BRS in FM patients. These results provide important information about the influence of BRS on pain chronicity. In addition to the evidence of baroreceptor-mediated modification of pain processing between groups or over longer periods of time, there is considerable evidence for a dynamic effect in which arterial baroreceptors modulate the processing of nociception during each cardiac cycle. Further, the unaltered pain thresholds, pain tolerance and BRS after stimulation that is independent of the cardiac cycle validates the effects observed after the SP-protocol and strongly suggest that the results found with the SP-protocol do not represent a simple placebo effect. The Non-SP-protocol can be considered to be a placebo control condition in this study. Consistent with diminished BRS, HRV measures of sympathetic and parasympathetic nervous system activity were significantly lower in FM patients than in HCs. The functional consequences of diminished BRS include impaired inhibition of sympathetic nervous system arousal responses and impaired activation of parasympathetic nervous system inhibitory responses evoked by stressful stimuli (Randich and Maixner, 1984). The overall sympathetic tone for the FM patients was significantly higher than the controls. The highest activation of the parasympathetic nervous system (HF) and the lowest activation of the sympathetic nervous system (LF) were found after the SP-protocol. Without being limited to any particular mechanism, these results suggest decreased sympathetic activity resulting from an increase in BRS produced by the delivery of the electrical stimuli during the systolic phase of the cardiac cycle in the SP-protocol and an effect on vagal activity. Decreased BRS is also associated with increased anxiety levels (Watkins et al 2002) and both acute (Dito et al 1990, Steptoe et al. 1993) and chronic stress (Lawler et al. 1991, Qian et al. 1997). Central noradrenergic mechanisms may account for the reduced BRS associated with chronic pain (Lawler et al. 1991, Mitchell and Lawler 1989). Possible interactive effects of substance P, mu-opioid receptor, and alpha-2 adrenergic activity in baroreceptor-mediated cardiovascular regulation, combined with chronic pain-related changes in pathways mediated by these neurochemicals, might also contribute to baroreceptor-mediated changes in the BP/pain sensitivity relationship in chronic pain. The reduction of baroreceptor sensitivity by acute and chronic stress, likely includes reduction by pain-related stress. The data provided herein indicate that the SP-protocol results in reduced sympathetic activity over the course of the treatment sessions and further that such a response can lead to a restoration of the physiological balance of the autonomic nervous system (parasympathetic and sympathetic) and an improvement in the clinical signs and symptoms of diseases and disorders that are influenced by reduced parasympathetic and/or increased sympathetic activity.

This effect of diminished BRS, high sympathetic tone, and vagal activation due to acute and chronic stress provides a physiological explanation for the influence of stress on disease. Thus, the SP-protocol may become a helpful intervention for multiple diseases influenced by stress.

Treatment.

The first treatment effects validated the theoretical approach. Pronounced treatment effects were obtained despite a reduction in the number of total treatment sessions (compared to OBT alone) of more than 30%. All patients treated with OBT and the SP-Protocol became pain-free during the 5 weekly treatments. Pain threshold and pain tolerance remained elevated by 50.01% and 111.37% 6-12 months after the treatment. Consistent with prolonged abolished pain, BRS was increased three-fold from pre-treatment levels. Hypertensive BP was increased in some subjects prior to treatment. Without being limited to any one mechanism, it is assumed that the increased BP prior to treatment may reflect an endogenous attempt at reactivation of the inverse BP/pain relationship. However, this reactivation is prevented by the diminished BRS caused by chronic stress that activates the noradrenergic pathway, increases BP and reduces HRV. The observed hypertensive BP was decreased after treatment with the SP-protocol. Without being limited to any one mechanism, stimulation administered immediately after the systolic peak of the cardiac cycle increases BP, when transmitted through the spinal nerve to the brain and also directly influences the cardiac system, reactivating the diminished BRS, which results in inhibition of the Ascending Reticular Activating System (ARAS, Maixner 1997; Bruehl & Chung, 2004); Bruehl et al., 1998)). As described in the Introduction, the ARAS is a non-specific, cortical projecting system (Randich and Maixner 1984, Dworkin et al. 1994) that originates from a diverse number of nuclear groups in the brain stem and basal forebrain (e.g., parabrachial nucleus, locus coeruleus, raphe system, nucleus basalis, etc) and plays an important role in sculpturing sensory, motor, and autonomic responses to somatosensory input (Steriade 1988, Steriade and Llinas 1988). The rostral part of the reticular formation has been described as the head of the autonomic nervous system (Rohen 1978) from which ascending input is transmitted to the lateral prefrontal and to the insular cortices (Bornhovd et al. 2002). The hypothalamus receives direct input from the Nucleus Tractus Solitarius (NTS), but also visceral information via the thalamus.

The thalamus receives baroreceptor input via the reticular formation. Rutecki (1990) suggests that the connection between the thalamus and the insular cortex mediates important visceral reflexes and this connection has been mentioned as the possible link to conscious perception of visceral sensations (Elbert and Schandry 1998). According to this concept, baroreceptors afferents originating from the carotid sinus and the heart/lungs project to the NTS and influence the NTS circuit in a way that alters the activity of the thalamus, insula, ACC, limbic system. Increases in arterial or venous BP activate baroreceptor afferents that sends signals to the NTS. Afferents that leave the NTS not only cause a suppression of pain transmission at the sites noted above, but send afferents to adjacent brainstem regions that cause a decrease in sympathetic activity and an increase in parasympathetic activity—resulting in a lowering of blood pressure and a decrease in HR. Without being limited to any one mechanism, during treatment and in reaction to the strong stimulation of the SP-protocol compared to the persistent stimulation of chronic pain, the sympathetic system resets to a lower level of sympathetic tone, thereby increasing BRS and restoring the sympathetic parasympathetic balance, reducing pain.

The OBT treatment focused on reduction of pain behaviors. Neuroimaging evidence suggests that pain interference of task performance caused by diverting attention away from the task is associated with a higher pain-related activations in the caudal and rostral anterior cingulate cortex (ACC) and ventroposterior thalamus while focusing on the task during painful stimulation, which presumably caused a reduction in pain-related activity or pain behaviors, is associated with pain-related activations in three different brain regions: primary (S1), and secondary (S2) somatosensory cortices, and anterior insula (Seminovicz et al., 2004). These results show that cognitive load can modulate pain-related cortical activity (Seminovicz et al., 2004) and both highlight the necessity of and demonstrate the mechanism of behavioral pain intervention.

OBT reduces pain behaviors and activates healthy behaviors and has demonstrated clinical significant reduction of pain and pain-related interference in 65% and 58% of patients 12 months after treatment in an inpatients and outpatient setting, especially (Thieme et al., 2003, 2006). These improvements in interference related to pain and pain severity were significantly associated with bilateral activation in pain evoked activity in the posterior insula, the ipsilateral caudate nucleus/striatum, the contralateral lenticular nucleus, the left thalamus and the primary somatosensory cortex contralateral to the stimulated side. These results strongly suggest a causal link between successful behavioral treatment and higher activation bilaterally in the posterior insula and in the contralateral primary somatosensory cortex (Diers et al., 2012).

Conclusion. The BRS mechanism is an important factor in pain chronicity and is associated with vagal activation and changes in brainstem and other parts of the pain network. The application of pain and pain-free stimuli after SP-Protocol decreases clinical pain by increasing pain threshold, pain tolerance, and BRS as well as parasympathetic activity based on classical and operant conditioning. Based on classical and operant conditioning, over time these new values are learned and the system is reset and altered such that pain is persistently reduced. Twenty treatment hours of OBT combined with the SP-Protocol improved clinical pain in FM, OA, TMJD, Migraine, and VVS, reduced BP hypertonia, removed sleep apnea and RLS and improved anxiety disorders based on increased vagal activity and increased descending inhibition and diminished facilatory activity resulting in reduction of central sensitization and temporal summation (Watkins and Mayer 1999, 1999a), and is also functionally involved in cardiovascular regulation (Ku et al. 1998, Seagard et al. 2000) by involving Substance P pathways and the brain structures such as NTS and NRM.

The results of the study show positive effects of OBT combined with the SP-Protocol on different chronic pain disorders such as FM, OA, TMJD, Migraine, VVS and RA. The positive effects in FM which are difficult to treat are dramatic with complete pain reduction in all treated patients. The treatment reduces systolic blood pressure hypertonia, and removes sleep apnea and RLS as well as anxiety disorders (Phobia and PTSD). Considering the tremendous influence on anxiety reduction, further studies should test if anxiety reduction in oncology patients might influence the reactivity of the immune system and improve survival rate.

TABLE 1

Baseline differences of sensory, pain and tolerance thresholds in FM and HC.

|  | FM (N = 32) | | HC (N = 30) | | | |
| --- | --- | --- | --- | --- | --- | --- |
|  | Mean | SEM | Mean | SEM | T | p |
| Sensory Threshold (µA) | 305.91 | 18.97 | 253.22 | 28.59 | 0.5771 | ns |
| Pain Threshold (µA) | 1035.15 | 92.17 | 1414.96 | 101.96 | 3.884 | <0.001 |
| Tolerance (µA) | 2632.12 | 167.52 | 3792.24 | 157.27 | 3.972 | <0.001 |

TABLE 2

Natural log Mean and SD's values of different HRV variables in FM patients and HC, differences between and within the groups during 5-minutes baseline, 8-minutes trial1 and trial2.

| | Groups | | | | | | | |
| --- | --- | --- | --- | --- | --- | --- | --- | --- |
| Variable | FM Mean (SD) | HC Mean (SD) | Sign Groups U | p | Sign FM Chi2 | p | Sign HC Chi2 | p |
| TP Baseline | 5.31 (1.10) | 6.62 (0.95) | 171.00 | <0.001 | 24.78 | <0.001 | 2.79 | ns. |
| SP1 | 6.48 (0.89) | 6.86 (0.76) | 240.00 | ns. | | | | |
| SP2 | 6.58 (0.86) | 6.72 (0.81) | 190.00 | ns. | | | | |
| P1 | 6.43 (0.77) | 6.82 (0.72) | 153.00 | 0.021 | 9.38 | 0.009 | 0.22 | ns. |
| P2 | 6.62 (0.96) | 6.63 (0.67) | 203.00 | ns. | | | | |
| Non_SP1 | 6.4 (0.74) | 6.79 (0.72) | 160.00 | (0.054) | 13.85 | 0.001 | 8.07 | 0.018 |
| Non_SP2 | 6.62 (0.79) | 6.82 (0.83) | 183.00 | ns. | | | | |
| HF Baseline | 2.08 (0.79) | 3.06 (0.93) | 188.00 | 0.001 | | | | |
| SP1 | 3.08 (1.38) | 3.11 (0.78) | 298.00 | ns. | | | | |
| SP2 | 2.98 (1.62) | 2.94 (0.75) | 247.00 | ns. | 9.44 | 0.014 | 2.64 | ns. |
| P1 | 2.63 (0.56) | 3.33 (1.06) | 177.00 | ns. | 11.69 | 0.003 | 0.67 | ns. |
| P2 | 2.65 (0.62) | 3.08 (0.89) | 152.00 | ns. | | | | |
| Non_SP1 | 2.62 (0.59) | 3.15 (0.89) | 172.00 | ns. | 13.86 | 0.001 | 0.67 | ns. |
| Non_SP2 | 2.87 (0.83) | 3.21 (1.03) | 161.00 | (0.057) | | | | |
| LF Baseline | 3.91 (1.13) | 5.03 (1.18) | 218.00 | 0.003 | 14.11 | 0.001 | 0.07 | ns. |
| SP1 | 4.96 (0.84) | 4.98 (0.87) | 296.00 | ns. | | | | |
| SP2 | 5.18 (1.05) | 5.01 (0.85) | 239.00 | ns. | | | | |
| P1 | 4.64 (0.85) | 5.02 (0.83) | 161.00 | ns. | 8.77 | 0.012 | 0.52 | ns. |
| P2 | 4.92 (1.02) | 4.97 (0.84) | 184.00 | ns. | | | | |
| Non_SP1 | 4.66 (1.01) | 5.10 (0.99) | 153.00 | 0.037 | 16.00 | <0.001 | 2.00 | ns. |
| Non_SP2 | 4.82 (0.92) | 5.09 (1.02) | 186.00 | ns. | | | | |
| VLF Baseline | 4.93 (0.83) | 6.07 (0.86) | 184.00 | <0.001 | 8.44 | 0.015 | 2.214 | ns. |
| SP1 | 5.64 (0.92) | 6.25 (0.77) | 189.00 | 0.020 | | | | |
| SP2 | 5.81 (0.91) | 6.16 (0.83) | 158.00 | 0.034 | | | | |

TABLE 2-continued

Natural log Mean and SD's values of different HRV variables in FM patients and HC, differences between and within the groups during 5-minutes baseline, 8-minutes trial1 and trial2.

| | Groups | | | | | | | |
|---|---|---|---|---|---|---|---|---|
| | FM Mean | HC Mean | Sign Groups | | Sign FM | | Sign HC | |
| Variable | (SD) | (SD) | U | p | Chi2 | p | Chi2 | p |
| P1 | 6.03 (0.80) | 6.15 (0.74) | 209.00 | ns. | | | | |
| P2 | 5.97 (0.88) | 6.05 (0.71) | 187.00 | ns. | 9.39 | 0.009 | 0.89 | ns. |
| Non_SP1 | 5.90 (0.79) | 6.21 (0.76) | 162.00 | ns. | 6.14 | ns. | 4.52 | ns. |
| Non_SP2 | 6.02 (0.86) | 6.24 (0.84) | 181.00 | ns. | | | | |
| SDNN Baseline | 2.73 (0.42) | 3.31 (0.47) | 164.00 | <0.001 | 21.38 | <0.001 | 2.00 | ns. |
| SP1 | 3.26 (0.44) | 3.42 (0.37) | 274.00 | ns. | | | | |
| SP2 | 3.29 (0.41) | 3.35 (0.39) | 227.00 | ns. | | | | |
| P1 | 3.22 (0.38) | 3.41 (0.35) | 175.00 | ns. | 9.38 | 0.009 | 0.96 | ns. |
| P2 | 3.30 (0.47) | 3.31 (0.34) | 225.00 | ns. | | | | |
| Non_SP1 | 3.22 (0.37) | 3.39 (0.36) | 157.00 | ns. | 13.29 | 0.001 | 8.29 | 0.016 |
| Non_SP2 | 3.30 (0.39) | 3.41 (0.42) | 185.00 | ns. | | | | |
| rmSSD Baseline | 1.68 (0.35) | 2.19 (0.44) | 208.00 | 0.002 | 16.63 | <0.001 | 1.14 | ns. |
| SP1 | 2.31 (0.77) | 2.20 (0.37) | 284.00 | ns. | | | | |
| SP2 | 2.39 (0.81) | 2.17 (0.33) | 236.00 | ns. | | | | |
| P1 | 2.66 (1.71) | 2.34 (0.52) | 184.00 | ns. | 22.80 | <0.001 | 0.29 | ns. |
| P2 | 2.66 (1.68) | 2.24 (0.45) | 201.00 | ns. | | | | |
| Non_SP1 | 2.65 (1.75) | 2.24 (0.40) | 207.00 | ns. | 16.13 | <0.001 | 1.185 | ns. |
| Non_SP2 | 1.99 (0.34) | 2.29 (0.54) | 152.00 | 0.035 | | | | |

REFERENCES

Banic B, Petersen-Felix St, Andersen O K, Radanov B P, Villiger P M, Arendt-Nielsen L, Curatolo M. Evidence for spinal cord hypersensitivity in chronic pain after whiplash injury and in fibromyalgia. Pain, 2004, 107: 7-15.

Berrino L, Oliva P, Rossi F, Palazzo E, Nobili B, Malone S. Interaction between metabotropic and NMDA glutamate receptors in the periaqueductal grey pain modulation system. Naunyn Schmiedebergs Archive of Pharmacology, 2001, 364: 437-443.

Berntson G G, Bigger J T Jr, Eckberg D L, Grossman P, Kaufmann P G, Malik M, Nagaraja H N, Porges S W, Saul J P, Stone P H, van der Molen M W. Heart rate variability: origins, methods, and interpretive caveats. Psychophysiology 1997, 34:623-48. Review.

Bornhovd K, Quante M, Glauche V, Bromm B, Weiller C, Buchel C. Painful stimuli evoke different stimulus-response functions in the amygdala, prefrontal, insula and somatosensory cortex: a single-trial fMRI study. Brain 2002, 125: 1326-1336.

Boucsein W: Elektrodermale Aktivität [Electrodermal activity]. Berlin, Heidelberg, N.Y.: Springer; 1988.

Burgmer M, Pfleiderer B, Maihoefner C, Gaubitz M, Wessoleck H, Heuft G, Pogatzki-Zahn E, Cerebral mechanisms of experimental hyperalgesia in fibromyalgia. Eur J Pain, 2012, 16(5): 636-647.

Bruehl S, Burns J W, McCubbin J A. Altered cardiovascular/pain regulatory relationships in chronic pain. Int J Behav Med 1998, 5, 63-75.

Bruehl, S. & Chung, O. Y. Interactions between the cardiovascular and pain regulatory systems: an updated review of mechanisms and possible alterations in chronic pain. Neurosci. Biobehav. Rev. 2004, 28: 395-414.

Diers M, Yilmaz P, Rance M, Thieme K, Gracely R H, Rolko C, Schley M T, Kiessling U, Wang H, Flor H. Treatment-related changes in brain activation in patients with fibromyalgia syndrome. Exp Brain Res. 2012, 218: 619-28.

Ditto B. France C. Carotid baroreflex sensitivity at rest and during psychological stress in offspring of hypertensives and non-twin sibling pairs. Psychosomatic Medicine 1990, 52: 610-620.

Edwards L, Inui K, Ring C, Wang X, Kakigi R. Pain-related evoked potentials are modulated across the cardiac cycle. Pain 2008, 137: 488-494.

Elbert T, Dworkin B R, Rau H, Pauli P, Birbaumer N, Droste C, Brunia C H. Sensory effects of baroreceptor activation and perceived stress together predict long-term blood pressure elevations. International Journal of Behavioral Medicine 1994, 1: 215-128.

Elbert T, Ray W J, Kowalik Z J, Skinner J E, Graf K E, Birbaumer N. Chaos and physiology: deterministic chaos in excitable cell assemblies. Physiological Review 1994a, 74: 1-47.

Elbert T, Rockstroh B, Lutzenberger W, Kessler M, Pietrowsky R. Baroreceptor stimulation alters pain sensation depending on tonic blood pressure. Psychophysiology 1988, 25(1): 25-29.

Elbert T, Schandry R I E. Wechselwirkungen zwischen kardiovaskulärem und zentralnervösem System [Interactions between cardiovascular and central nervous system]. Enzyklopädie der Psychologie, Serie Biologische Psychologie [Encyclopedia of Psychology, Biological Psychology]. F. Roesler. Göttingen, Hogrefe 1998: 427-477.

Flor H, Birbaumer N: Psychobiologie und interdisziplinäre Therapie chronischer Wirbelsäulensyndrome [Psychobiology and Interdisciplinary Treatment of Chronic Back Pain] München: GSF Forschungszentrum; 1994.

Flor H, Knost B, Birbaumer N. The role of operant conditioning in chronic pain: an experimental investigation. Pain 2002, 95(1-2): 111-118.

Flor H, Birbaumer N. Acquisition of chronic pain: Psychophysiological mechanisms. American Pain Society Journal 1994a, 3: 119-127.

Fridlund A J, Cacioppo J T: Guidelines for human electromyographic research. Psychophysiology. 1986; 23:567-89.

Gracely R H, Petzke F, Wolf J M, Clauw D J. Functional magnetic resonance imaging evidence of augmented pain processing in fibromyalgia. Arthritis Rheum 2002, 46(5): 1333-43.

Graven-Nielsen T, Aspegren Kendall S, Henriksson K G, Bengtsson M, Sörensen J, Johnson A, Gerdle B, Arendt-Nielsen L. Ketamine reduces muscle pain, temporal summation, and referred pain in fibromyalgia patients. Pain 2000, 85(3):483-91.

Jennings J R, Berg W K, Hutcheson J S, Obrist P, Porges S, Turpin G: Committee report. Publication guidelines for heart rate studies in man. Psychophysiology. 1981; 18:226-31.

Jensen K B, Kosek E, Wicksell R, Kemani M, Olsson G, Merle J V, Kadetoff D, Ingvar M. Cognitive Behavioral Therapy increases pain-evoked activation of the prefrontal cortex in patients with fibromyalgia. Pain 2012, 153: 1495-1503.

Kircher T, Arolt V, Jansen A, Pyka M, Reinhardt I, Kellermann T, Konrad C, Lueken U, Gloster A T, Gerlach A L, Strohle A, Wittmann A, Pfleiderer B, Wittchen H U, Straube B. Effect of cognitive-behavioral therapy on neural correlates of fear conditioning in panic disorder. Biol Psychiatry 2013, 73:93-101.

Ku Y H, Tan L, Li L S, Ding X. Role of corticotropin-releasing factor and substance P in pressor responses of nuclei controlling emotion and stress. *Peptides* 1998, 19: 677-682.

Lawler J E, Sanders B J, Cox R H, O'Connor E F. Baroreflex function in chronically stressed borderline hypertensive rats. Physiological Behavior 1991, 49: 539-542.

Maixner W. Interactions between cardiovascular and pain modulatory systems: physiological and pathophysiological implications. J Cardiovas Electrophysiol (Suppl.) 1991, 2: S2-S12.

Maixner W, Fillingim R, Kincaid S, Sigurdsson A, Harris M B. Relationship between pain sensitivity and resting arterial blood pressure in patients with painful temporomandibular disorders. Psychosom Med 1997, 59: 503-511.

Maixner W, Sigurdsson A, Fillingim R, Lundeen T, Booker D. Regulation of acute and chronic orofacial pain. In: Orofacial Pain and Temporomandibular Disorders (eds Fricton J R & Dubner R B) 85-102 (Raven Press, Ltd, New York, 1995).

McIntyre D, Edwards L, Ring C, Parvin B, Carroll D. Systolic inhibition of nociceptive responding is moderated by arousal. Psychophysiology 2006, 43: 314-9.

Mitchell V P, Lawler J E. Norepinephrine content of discrete brain nuclei in acutely and chronically stressed borderline hypertensive rats. Brain Research Bulletin 1989, 22: 545-547.

Okifuji A, Turk D C, Sinclair J D, Starz T W, Marcus D A. A standardized manual tender point survey: I. Development and determination of a threshold point for the identification of positive tender points in fibromyalgia syndrome. J Rheumatol 1997, 24:377-383.

Moher D, Schulz K F, Altman D G, for the CONSORT Group. The CONSORT statement: revised recommendations for improving the quality of reports of parallel-group randomized trials. Lancet 2001, 357:1191-1194.

Pertovaara A. A neuronal correlate of secondary hyperalgesia in the rat spinal dorsal horn is submodality selective and facilitated by supraspinal influence. Experimental Neurology 1998, 149: 193-202.

Qian Z M, X D, Huang W Q, Tang P L, Xu B. Central ANG II receptor involved in carotid sinus reflex resetting in chronically stressed rats. Physiological Behavior 1997, 62: 241-247.

Randich A, Maixner W. Interactions between cardiovascular and pain regulatory systems. Neuroscience & Biobehavioral Review 1984, 8: 343-367.

Rau H, Elbert T. Psychophysiology of arterial baroreceptors and the etiology of hypertension. Biological Psychiatry 2001, 57: 179-201.

Rau H, Pauli P, Brody S, Elbert T, Birbaumer N. Baroreceptor stimulation alters cortical activity. Psychophysiology 1993, 30: 322-325.

Rohen J W. Functional anatomy of nervous system. Stuttgart, Schattauer, 1978.

Rutecki P. Anatomical, physiological, and theoretical basis for the antiepileptic effect of vagus nerve stimulation. Epilepsia 1990, 31: S1-S6.

Seagard J L, Dean C, Hopp F A. Modulation of the carotid baroreceptor reflex by substance P in the nucleus tractus solitarius. Journal of Autonomic Nervous System 2000, 78: 77-85.

Seminowicz D A, Mikulis D J, Davis K D. Cognitive modulation of pain-related brain responses depends on behavioral strategy. Pain 2004, 112: 48-58.

Staud R, Price D D, Robinson M E, Mauderli A P, Vierck C J. Maintenance of windup of second pain requires less frequent stimulation in fibromyalgia patients compared to normal controls. Pain 2004, 110: 689-696.

Steptoe A, Sawada Y. Assessment of baroreceptor reflex function during mental stress and relaxation. Psychophysiology 1978, 26:140-147.

Steriade M. New vistas on the morphology, chemical transmitters and physiological actions of the ascending brainstem reticular system. Archives Italiennes de Biologie 1988, 126: 225-238.

Steriade M, Llinas R R. The functional states of the thalamus and the associated neuronal interplay. Physiology Review 1988, 68: 649-742.

Thieme K, Flor H, Turk D C. Psychological pain treatment in fibromyalgia syndrome: Efficacy of operant- and cognitive-behavioral treatments in Fibromyalgia Syndrome. Arthritis Research & Therapy; 2006, 8:R121 (1-12).

Thieme K, Gromnica-Ihle E, Flor H. Operant behavioral treatment of fibromyalgia: a controlled study. Arthritis Rheum 2003, 49:314-320.

Thieme, K., Turk, D. C. (2006). Heterogeneity of psychophysiological stress responses in fibromyalgia syndrome patients. Arthritis Research & Therapy 8: R9.

Thieme K, Turk D C, Flor H. Responder criteria for operant and cognitive-behavioral treatment of fibromyalgia syndrome. Arthritis & Rheumatism/Arthritis Care & Res, 2007, 57:830-6.

Vlaeyen J W, Haazen I W, van Schuerman J A, Kole-Snijders A M, Eek H. Behavioral rehabilitation of chronic low back pain: comparison of an operant treatment, an operant-cognitive treatment and an operant-respondent treatment. Br J Clin Psych 1995, 34: 95-118.

Watkins L L, Blumethal J A, Carney R M. Association of anxiety with reduced baroreflex cardiac control in patients after acute myocardial infarction. American Heart Journal 2002, 143:460-6.

Watkins L R, Maier S F. Cytokines and pain: progress in inflammation research. Boston, Birkhauser, 1999.

Watkins L R, Maier S F. Implications of immune-to-brain communication for sickness and pain. Proceedings of the National Academy of Sciences of the United States of America 1999a, 96: 7710-7713.

Wirtelak E P, Roemer B, Maier S F, Watkins L R. Comparison of the effects of nucleus tractus solitarius and ventral medial medulla lesions on illness-induced and subcutaneous formalin-induced hyperalgesia. Brain Research, 1997, 748:143-50.

Wolfe F, Clauw D J, Fitzcharles M A, Goldenberg D L, Hauser W, Katz R S, Mease P, Russell A S, Russell I J, Winfield J B. Fibromyalgia criteria and severity scales for clinical and epidemiological studies: a modification of the ACR Preliminary Diagnostic Criteria for Fibromyalgia. J Rheumatol. 2011, 38:1113-22.

Wolfe F, Smythe H A, Yunus M B, Bennett R M, Bombardier C, Goldenberg D L, Tugwell P, Campbell S M, Abeles M, Clark P, et al.: The American College of Rheumatology 1990 criteria for the classification of fibromyalgia. Report of the Multicenter Criteria Committee. Arthritis Rheum 1990, 33:160-172.

Woolf C J. Central sensitization: implications for the diagnosis and treatment of pain. Pain 2011, 152 (suppl): S2-S15).

What is claimed is:

1. A method for reducing pain in a subject comprising:
   delivering to a subject with a stimulator a series of stimuli, wherein at least a fraction of the stimuli are below a non-painful threshold for the subject and at least a fraction of the stimuli are 50% to 100% of a pain tolerance for the subject, and wherein a portion of each of the non-painful stimuli and the 50% to 100% of the pain tolerance stimuli is delivered during the systolic phase of the subject's cardiac cycle and the remaining portion of each is delivered during a diastolic phase of the subject's cardiac cycle.

2. The method of claim 1, further comprising repeating one or more times delivering to the subject the series of stimuli, until the subject's pain is reduced.

3. The method of claim 1, further comprising:
   repeating one or more times the delivering to the subject the series of stimuli to the subject, wherein the stimuli having the non-painful threshold and 50% to 100% of the pain tolerance are re-determined for the subject prior to the repeating delivery, until the subject's pain is reduced.

4. The method of claim 1, wherein the subject is characterized by one or more of fibromyalgia syndrome, migraine, osteoarthritis, low back pain, inflammatory arthritis, rheumatoid arthritis, or Parkinson's.

5. The method of claim 1, wherein the portion of each of the non-painful stimuli and the 50% to 100% of the pain tolerance stimuli delivered during the systolic phase is one half.

6. The method of claim 1, wherein the stimuli delivered during the systolic phase of the cardiac cycle are delivered at a 20% value of an average inter-beat-interval and the stimuli delivered during the diastolic phase of the cardiac cycle are delivered at an 80% value of an average inter-beat-interval.

7. The method of claim 1, wherein the stimulus is selected from the group consisting of an electrical pulse stimulus, a punctate stimulus, and a laser stimulus.

8. The method of claim 1, wherein the stimulus is an electrical pulse stimulus delivered as a train consisting of multiple individual electrical pulses of the same amplitude.

9. A device, comprising:
   a sensor for measuring cardiac cycle configured to indicate a systolic phase and a diastolic phase of a subject's cardiac cycle;
   a stimulator configured to deliver a stimulus to the subject; and
   a control module in communication with the sensor for measuring cardiac cycle and the stimulator, the control module configured to:
     direct the stimulator to deliver a series of the stimuli to the subject, wherein at least a fraction of the stimuli are below a non-painful threshold for the subject and at least a fraction of the stimuli are 50% to 100% of a pain tolerance for the subject, and wherein a portion of each of the non-painful stimuli and the 50% to 100% of the pain tolerance stimuli is delivered during the systolic phase of the subject's cardiac cycle and the remaining portion of each is delivered during the diastolic phase of the subject's cardiac cycle.

10. The device of claim 9, wherein the control module is configured to direct the stimulator to repeat one or more times the deliver function of the series of stimuli, until the subject's pain is reduced.

11. The device of claim 9, wherein the control module is configured to direct the stimulator to repeat one or more times the deliver function to the subject the series of stimuli to the subject, wherein the stimuli having the non-painful threshold and having 50% to 100% of the pain tolerance are re-determined for the subject prior to the repeated deliver function, until the subject's pain is reduced.

12. The device of claim 9, wherein the portion of each of the non-painful stimuli and the 50% to 100% of the pain tolerance stimuli delivered during the systolic phase is one half.

13. The device of claim 9, wherein the stimuli delivered during the systolic phase of the cardiac cycle are delivered at a 20% value of an average inter-beat-interval and the stimuli delivered during the diastolic phase of the cardiac cycle are delivered at an 80% value of an average inter-beat-interval.

14. The device of claim 9, wherein the stimulus is selected from the group consisting of an electrical pulse stimulus, a punctate stimulus, and a laser stimulus.

15. The device of claim 9, wherein the stimulus is an electrical pulse stimulus delivered as a train consisting of multiple individual electrical pulses of the same amplitude.

16. The device of claim 9, wherein the device facilitates pharmacotherapy in the subject by one or more of: enabling reduced dose of chemotherapy in the subject having melanoma, enabling reduced dose of antiepileptic drugs in the subject having epilepsy, enabling reduced dose of anti-inflammatory drugs in the subject having arthritis, enabling reduced dose of sleep-inducing drugs in the subject having sleep apnea, enabling reduced dose of detoxification drugs in the subject having chronic pain and opioid addiction, enabling reduced dose of anesthesia in the subject during surgery, enabling reduced dose of blood pressure-lowering drugs in the subject having hypertension, or enabling reduced dose of anti-anxiety drugs in the subject having anxiety.

17. A control module in communication with a sensor for measuring cardiac cycle configured to indicate a systolic phase and a diastolic phase of the subject's cardiac cycle and a stimulator, the control module configured to:
  direct the stimulator to deliver a series of stimuli to a subject, wherein at least a fraction of the stimuli are below a non-painful threshold for the subject and at least a fraction of the stimuli are 50% to 100% of a pain tolerance for the subject, and wherein a portion of each of the non-painful stimuli and the 50% to 100% of the pain tolerance stimuli is delivered during the systolic phase of the subject's cardiac cycle and the remaining portion of each is delivered during the diastolic phase of the subject's cardiac cycle.

18. The control module of claim 17, wherein the control module is configured to direct the stimulator to repeat one or more times the deliver function of the series of stimuli to the subject, until the subject's pain is reduced.

19. The control module of claim 17, wherein the control module is configured to direct the stimulator to repeat one or more times the deliver function of the series of stimuli to the subject, wherein the stimuli having the non-painful threshold and 50% to 100% of the pain tolerance are re-determined for the subject prior to the repeated deliver function, until the subject's pain is reduced.

20. A computer program product for reducing pain in a subject, comprising:
  a non-transitory computer readable storage medium having computer readable program code embodied therewith, the computer readable program code comprising:
  computer readable program code configured to:
    receive a response signal from a sensor for measuring cardiac cycle that indicates a systolic phase and a diastolic phase of a subject's cardiac cycle;
    direct a stimulator to deliver a series of stimuli to the subject, wherein at least a fraction of the stimuli are below a non-painful threshold for the subject and at least a fraction of the stimuli are 50% to 100% of a pain tolerance for the subject, and wherein a portion of each of the non-painful stimuli and the 50% to 100% of the pain tolerance stimuli is delivered during the systolic phase of the subject's cardiac cycle and the remaining portion of each is delivered during the diastolic phase of the subject's cardiac cycle.

21. The computer program product of claim 20, wherein the computer readable program code is further configured to direct the stimulator to repeat one or more times the deliver function of the series of stimuli to the subject, until the subject's pain is reduced.

22. The computer program product of claim 20, wherein the computer readable program code is further configured to direct the stimulator to repeat one or more times the deliver function of the series of stimuli to the subject, wherein the stimuli having the non-painful threshold and the 50% to 100% of the pain tolerance are re-determined for the subject prior to the repeated deliver function, until the subject's pain is reduced.

* * * * *